United States Patent
Davis et al.

(10) Patent No.: US 8,927,697 B2
(45) Date of Patent: Jan. 6, 2015

(54) PD-1 SPECIFIC ANTIBODIES AND USES THEREOF

(75) Inventors: Simon Davis, Oxon (GB); Kerry Louise Tyson, Berkshire (GB)

(73) Assignee: Isis Innovation Limited, Oxford (GB)

(*) Notice: Subject to any disclaimer, the term of this patent is extended or adjusted under 35 U.S.C. 154(b) by 826 days.

(21) Appl. No.: 13/062,559

(22) PCT Filed: Sep. 14, 2009

(86) PCT No.: PCT/IB2009/006946
§ 371 (c)(1),
(2), (4) Date: Mar. 7, 2011

(87) PCT Pub. No.: WO2010/029435
PCT Pub. Date: Mar. 18, 2010

(65) Prior Publication Data
US 2011/0171215 A1     Jul. 14, 2011

Related U.S. Application Data

(60) Provisional application No. 61/096,485, filed on Sep. 12, 2008.

(51) Int. Cl.
*C12P 21/08*     (2006.01)
*C07K 16/28*     (2006.01)
*A61K 39/00*     (2006.01)

(52) U.S. Cl.
CPC ........ *C07K 16/2818* (2013.01); *A61K 2039/505* (2013.01); *C07K 2316/95* (2013.01); *C07K 2317/56* (2013.01); *C07K 2317/565* (2013.01); *C07K 2317/73* (2013.01); *C07K 2317/34* (2013.01)
USPC ..................................................... 530/387.3

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 7,365,167 | B2 * | 4/2008 | Watkins et al. ............ 530/387.3 |
| 2004/0152871 | A1 * | 8/2004 | Nakajima et al. ............ 530/350 |
| 2006/0088521 | A1 | 4/2006 | Mahadevan |
| 2007/0202100 | A1 | 8/2007 | Wood et al. |

FOREIGN PATENT DOCUMENTS

WO     WO 2004/056875         7/2004
WO     WO 2004056875 A1 *     7/2004

OTHER PUBLICATIONS

George et al. (Circulation. 1998; 97: 900-906).*
Mariuzza et al. (Annu. Rev. Biophys. Biophys. Chem. 1987; 16: 139-159).*
Gussow et al (Methods in Enzymology. 1991; 203: 99-121).*
Greenspan et al. (Nature Biotechnology. 1999; 7: 936-937).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
[Fundamental Immunology p. 242 (William E. Paul, M.D. ed., 3d ed; 1993].*
Lippincott-Schwartz (Current Protocols in Cell Biology, 16.0.1-16.0.2, 2002).*
Wang, L. et al. "Programmed cell death 1 (PD-1) and its ligand PD-L1 are required for allograft tolerance" *European Journal of Immunology*, Oct. 1, 2007, pp. 2983-2990, vol. 37, No. 10.
Seko, Y. et al. "Roles of programmed death-1 (PD-1)/PD-1 ligands pathway in the development of murine acute myocarditis caused by coxsackievirus B3" *Cardiovascular Research*, Jun. 7, 2007, pp. 158-167, vol. 75, No. 1.
Finger, L. R. et al. "The human PD-1 gene: complete cDNA, genomic organization, and developmentally regulated expression in B cell progenitors" *GENE An International Journal on Genes and Genomes*, Sep. 15, 1997, pp. 177-187, vol. 197, No. 1-2.
Carreno, B. M. et al. "Therapeutic opportunities in the B7/CD28 family of ligands and receptors" *Current Opinion in Pharmacology*, Aug. 1, 2005, pp. 424-430, vol. 5, No. 4.
Davies, J. et al. "Affinity improvement of single antibody VH domains: residues in all three hypervariable regions affect antigen binding" *Immunotechnology*, Sep. 1, 1996, pp. 169-179, vol. 2, No. 3.
Holt, L. J. et al. "Domain antibodies: proteins for therapy" *TRENDS in Biotechnology*, Nov. 1, 2003, pp. 484-490, vol. 21, No. 11.
Zhang, X. et al. "Structural and Functional Analysis of the Costimulatory Receptor Programmed Death-1" *Immunity*, Mar. 1, 2004, pp. 337-347, vol. 20, No. 3.
Jones, P. T. et al. "Replacing the complementarity-determining regions in a human antibody with those from a mouse" *Nature*, May 29, 1986, pp. 522-525, vol. 321.
Riechmann, L. et al. "Reshaping human antibodies for therapy" *Nature*, Mar. 24, 1988, pp. 323-327, vol. 332.
Verhoeyen, M. et al. "Reshaping Human Antibodies: Grafting an Antilysozyme Activity" *Science*, Mar. 25, 1988, pp. 1534-1536, vol. 239.
Davis, S. J. et al. "The role of charged residues mediating low affinity protein-protein recognition at the cell surface by CD2" *Proc. Natl. Acad. Sci. USA.*, May 1998, pp. 5490-5494, vol. 95.

* cited by examiner

*Primary Examiner* — Brad Duffy
(74) *Attorney, Agent, or Firm* — Saliwanchik, Lloyd & Eisenschenk

(57) ABSTRACT

One aspect of the present disclosure provides antibodies that can act as agonists of PD-1, thereby modulating immune responses regulated by PD-1. Another aspect of the disclosure provides compositions comprising PD-1 specific antibodies and their use in methods of down regulating the immune response. These methods can be practiced on any subject, including humans or animals. Anti-PD-1 antibodies disclosed herein may be used, in another aspect of the invention, to detect PD-1 or its fragments in a biological sample. The amount of PD-1 detected may be correlated with the expression level of PD-1, and associated with the activation status of immune cells (e.g., activated T cells, B cells, and/or monocytes) in the subject.

10 Claims, 12 Drawing Sheets

| OKT3 | IgG1 (antiPD-1) |
|---|---|
| 148* | - |
| 574 | 31477 (Clone19) |
| 479 | 44358 (Clone 10) |
| | |
| 1601 | - |
| 1704 | 38883 (Clone 19) |
| 1754 | 51252 (Clone 10) |

* Numbers of molecules/bead

% Proliferation

|  | *In vitro* | *In vivo* |
|---|---|---|
| Clone 10 (weak signaling) | | |
| Clone 19 (strong signaling) | | |

FIG. 11A Single anti-homodimer mAb
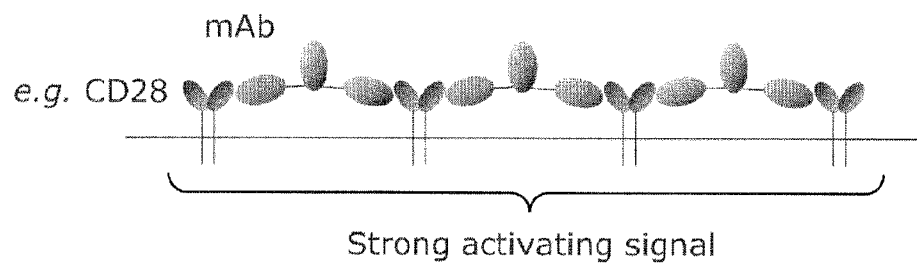
FIG. 11B Single anti-monomer mAb
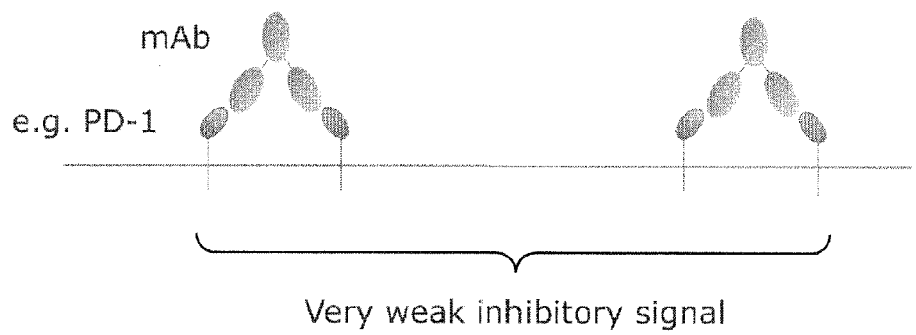
FIG. 11C Two anti-monomer mAbs binding to two non-overlapping epitopes
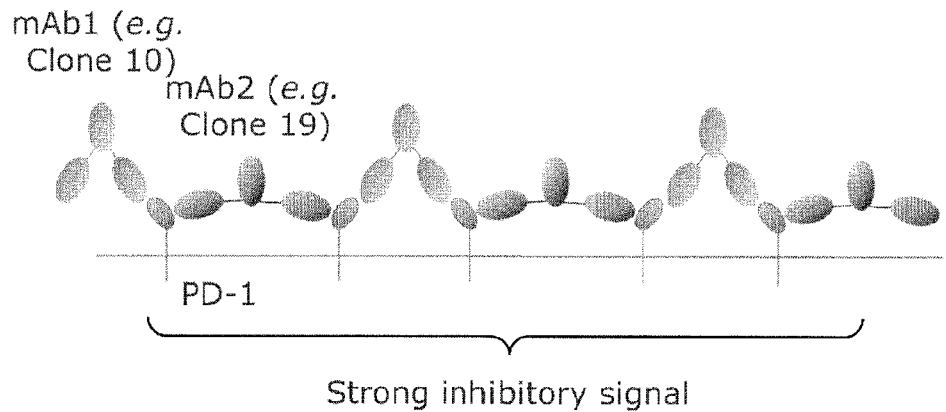

SEQUENCE LISTING

```
<160> NUMBER OF SEQ ID NOS: 38

<210> SEQ ID NO 1
<211> LENGTH: 333
<212> TYPE: DNA
<213> ORGANISM: Mus musculus
<220> FEATURE:
<221> NAME/KEY: CDS
<222> LOCATION: (1)..(333)
<220> FEATURE:
<221> NAME/KEY: misc_feature
<222> LOCATION: (1)..(333)
<223> OTHER INFORMATION: Clone 2 Vk (polynucleotide and polypeptide
      sequences)

<400> SEQUENCE: 1 gac att gtg ctg aca cag tct cct gct tct tta gct gta tct ctg ggg     48
Asp Ile Val Leu Thr Gln Ser Pro Ala Ser Leu Ala Val Ser Leu Gly
 1               5                  10                  15 cag agg gcc acc atc tca tgc agg gcc agc aaa agt gtc agt aca tct     96
Gln Arg Ala Thr Ile Ser Cys Arg Ala Ser Lys Ser Val Ser Thr Ser
             20                  25                  30 ggc ttt aat tat ata cac tgg tac caa cag aaa cca gga cag cca ccc    144
Gly Phe Asn Tyr Ile His Trp Tyr Gln Gln Lys Pro Gly Gln Pro Pro
         35                  40                  45 aaa ctc ctc atc tat ctt gca tcc aac cta gaa tct ggg gtc cct gcc    192
Lys Leu Leu Ile Tyr Leu Ala Ser Asn Leu Glu Ser Gly Val Pro Ala
     50                  55                  60 agg ttc agt ggc agt ggg tct ggg aca gac ttc acc ctc aac atc cat    240
Arg Phe Ser Gly Ser Gly Ser Gly Thr Asp Phe Thr Leu Asn Ile His
 65                  70                  75                  80 cct gtg gag gac gag gat gct gca acc tat tac tgt cag cac agt agg    288
Pro Val Glu Asp Glu Asp Ala Ala Thr Tyr Tyr Cys Gln His Ser Arg
                 85                  90                  95 gag ctt ccg ctc acg ttc ggt gct ggg acc aag ctg gaa ata aaa        333
Glu Leu Pro Leu Thr Phe Gly Ala Gly Thr Lys Leu Glu Ile Lys
            100                 105                 110
```

<210> SEQ ID NO 2
<211> LENGTH: 111
<212> TYPE: PRT
<213> ORGANISM: Mus musculus

<400> SEQUENCE: 2

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Phe Asn Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Glu Asp Ala Ala Thr Tyr Tyr Cys Gln His Ser Arg
                85                  90                  95

Glu Leu Pro Leu Thr Phe Gly Ala Gly Thr Lys Leu Glu Ile Lys
            100                 105                 110
```

<210> SEQ ID NO 3
<211> LENGTH: 354
<212> TYPE: DNA
<213> ORGANISM: Mus musculus
<220> FEATURE:
<221> NAME/KEY: CDS
<222> LOCATION: (1)..(354)
<220> FEATURE:
<221> NAME/KEY: misc_feature
<222> LOCATION: (1)..(354)
<223> OTHER INFORMATION: Clone 2 VH (polynucleotide and polypeptide
      sequences)

<400> SEQUENCE: 3

```
cag gtc caa ctg cag cag cct ggg gct gaa ctg gtg aag cct ggg gct      48
Gln Val Gln Leu Gln Gln Pro Gly Ala Glu Leu Val Lys Pro Gly Ala
1               5                   10                  15 tca gtg aag ttg tcc tgc aag gct tct ggc tac acc ttc acc acc tac      96
Ser Val Lys Leu Ser Cys Lys Ala Ser Gly Tyr Thr Phe Thr Thr Tyr
            20                  25                  30 tat ttg tac tgg gtg agg cag agg cct gga caa ggc ctt gag tgg att     144
Tyr Leu Tyr Trp Val Arg Gln Arg Pro Gly Gln Gly Leu Glu Trp Ile
        35                  40                  45 ggg ggg att aat cct agc aat ggt ggt act aac ttc aat gag aag ttc     192
Gly Gly Ile Asn Pro Ser Asn Gly Gly Thr Asn Phe Asn Glu Lys Phe
    50                  55                  60 aag agc aag gcc aca ctg act gta gac aaa tcc tcc agc aca gcc tac     240
Lys Ser Lys Ala Thr Leu Thr Val Asp Lys Ser Ser Ser Thr Ala Tyr
65                  70                  75                  80 atg caa ctc aac agc ctg aca tct gag gac tct gcg gtc tat tac tgt     288
Met Gln Leu Asn Ser Leu Thr Ser Glu Asp Ser Ala Val Tyr Tyr Cys
                85                  90                  95 aca aga cgg gac tat agg tac gac aga ggc ttt gac tac tgg ggc caa     336
Thr Arg Arg Asp Tyr Arg Tyr Asp Arg Gly Phe Asp Tyr Trp Gly Gln
            100                 105                 110 ggc acc tca gtc aca gtc                                             354
Gly Thr Ser Val Thr Val
            115
```

```
<210> SEQ ID NO 4
<211> LENGTH: 118
<212> TYPE: PRT
<213> ORGANISM: Mus musculus

<400> SEQUENCE: 4

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Tyr Leu Tyr Trp Val Arg Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Thr Arg Arg Asp Tyr Arg Tyr Asp Arg Gly Phe Asp Tyr Trp Gly Gln
            100                 105                 110

Gly Thr Ser Val Thr Val
        115

<210> SEQ ID NO 5
<211> LENGTH: 354
<212> TYPE: DNA
<213> ORGANISM: Artificial Sequence
<220> FEATURE:
<223> OTHER INFORMATION: Clone 2 VH mutated splice site (polynucleotide
      and polypeptide sequences)
<220> FEATURE:
<221> NAME/KEY: CDS
<222> LOCATION: (1)..(354)

<400> SEQUENCE: 5 cag gtc caa ctg cag cag cct ggg gct gaa ctg gtg aag cct ggg gct      48
Gln Val Gln Leu Gln Gln Pro Gly Ala Glu Leu Val Lys Pro Gly Ala
1               5                   10                  15 tca gtg aag ttg tcc tgc aag gct tct ggc tac acc ttc acc acc tac      96
Ser Val Lys Leu Ser Cys Lys Ala Ser Gly Tyr Thr Phe Thr Thr Tyr
            20                  25                  30 tat ttg tac tgg gtg agg cag agg cct gga caa ggc ctt gag tgg att     144
Tyr Leu Tyr Trp Val Arg Gln Arg Pro Gly Gln Gly Leu Glu Trp Ile
        35                  40                  45 ggg ggg att aat cct agc aat ggt ggt act aac ttc aat gag aag ttc     192
Gly Gly Ile Asn Pro Ser Asn Gly Gly Thr Asn Phe Asn Glu Lys Phe
    50                  55                  60 aag agc aag gcc aca ctg act gta gac aaa tcc tcc tct aca gcc tac     240
Lys Ser Lys Ala Thr Leu Thr Val Asp Lys Ser Ser Ser Thr Ala Tyr
65                  70                  75                  80 atg caa ctc aac agc ctg aca tct gag gac tct gcg gtc tat tac tgt     288
Met Gln Leu Asn Ser Leu Thr Ser Glu Asp Ser Ala Val Tyr Tyr Cys
                85                  90                  95 aca aga cgg gac tat agg tac gac aga ggc ttt gac tac tgg ggc caa     336
Thr Arg Arg Asp Tyr Arg Tyr Asp Arg Gly Phe Asp Tyr Trp Gly Gln
            100                 105                 110 ggc acc tca gtc aca gtc                                             354
Gly Thr Ser Val Thr Val
        115
```

```
<210> SEQ ID NO 6
<211> LENGTH: 118
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Tyr Leu Tyr Trp Val Arg Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Ser Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Thr Arg Arg Asp Tyr Arg Tyr Asp Arg Gly Phe Asp Tyr Trp Gly Gln
            100                 105                 110

Gly Thr Ser Val Thr Val
        115

<210> SEQ ID NO 7
<211> LENGTH: 336
<212> TYPE: DNA
<213> ORGANISM: Mus musculus
<220> FEATURE:
<221> NAME/KEY: CDS
<222> LOCATION: (1)..(336)
<220> FEATURE:
<221> NAME/KEY: misc_feature
<222> LOCATION: (1)..(336)
<223> OTHER INFORMATION: Clone 10 Vk (polynucleotide and polypeptide
      sequences)

<400> SEQUENCE: 7 gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct ggt cag aac att gta cat agt      96
Asp Gln Ala Ser Ile Ser Cys Arg Ser Gly Gln Asn Ile Val His Ser
            20                  25                  30 aat gga aac acc tat tta gaa tgg tac cta cag aaa cca ggc cag tct     144
Asn Gly Asn Thr Tyr Leu Glu Trp Tyr Leu Gln Lys Pro Gly Gln Ser
        35                  40                  45 cca aag ctc ctg atc tac aaa gtc tcc aac cga ttt ttt ggg gtc cca     192
Pro Lys Leu Leu Ile Tyr Lys Val Ser Asn Arg Phe Phe Gly Val Pro
    50                  55                  60 gac agg atc agt ggc agt gga tca ggg aca gat ttc aca ctc aag atc     240
Asp Arg Ile Ser Gly Ser Gly Ser Gly Thr Asp Phe Thr Leu Lys Ile
65                  70                  75                  80 agc aga gtg gag gct gag gat ctg gga gtt tat ttc tgc ttt caa ggt     288
Ser Arg Val Glu Ala Glu Asp Leu Gly Val Tyr Phe Cys Phe Gln Gly
                85                  90                  95 tca cat gtt cca ttc acg ttc ggc tcg ggg aca aag ctg gaa ata aaa     336
Ser His Val Pro Phe Thr Phe Gly Ser Gly Thr Lys Leu Glu Ile Lys
            100                 105                 110
```

<210> SEQ ID NO 8
<211> LENGTH: 112
<212> TYPE: PRT
<213> ORGANISM: Mus musculus

<400> SEQUENCE: 8

```
Asp Val Leu Met Thr Gln Thr Pro Leu Ser Leu Pro Val Ser Leu Gly
1               5                   10                  15

Asp Gln Ala Ser Ile Ser Cys Arg Ser Gly Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 9
<211> LENGTH: 354
<212> TYPE: DNA
<213> ORGANISM: Mus musculus
<220> FEATURE:
<221> NAME/KEY: CDS
<222> LOCATION: (1)..(354)
<220> FEATURE:
<221> NAME/KEY: misc_feature
<222> LOCATION: (1)..(354)
<223> OTHER INFORMATION: Clone 10 VH (polynucleotide and polypeptide sequences)

<400> SEQUENCE: 9

```
gat gtg cag ctt cag gag tcg gga cct ggc ctg gtg aaa cct tct cag      48
Asp Val Gln Leu Gln Glu Ser Gly Pro Gly Leu Val Lys Pro Ser Gln
1               5                   10                  15 tct ctg tcc ctc acc tgc act gtc act ggc tac tca atc acc agt gat      96
Ser Leu Ser Leu Thr Cys Thr Val Thr Gly Tyr Ser Ile Thr Ser Asp
            20                  25                  30 tat gcc tgg aac tgg atc cgg cag ttt cca gga aac aaa ctg gag tgg     144
Tyr Ala Trp Asn Trp Ile Arg Gln Phe Pro Gly Asn Lys Leu Glu Trp
        35                  40                  45 atg ggc tac ata aac tac agt ggt agc act agc tac aac cca tct ctc     192
Met Gly Tyr Ile Asn Tyr Ser Gly Ser Thr Ser Tyr Asn Pro Ser Leu
    50                  55                  60 aaa agt cga atc tct atc act cga gac aca tcc aag aac cag ttc ttc     240
Lys Ser Arg Ile Ser Ile Thr Arg Asp Thr Ser Lys Asn Gln Phe Phe
65                  70                  75                  80 ctg cag ttg aat tct gtg act act gag gac aca gcc aca tat tac tgt     288
Leu Gln Leu Asn Ser Val Thr Thr Glu Asp Thr Ala Thr Tyr Tyr Cys
                85                  90                  95 gca aga tgg atc ggt agt agc gcc tgg tac ttc gat gtc tgg ggc gca     336
Ala Arg Trp Ile Gly Ser Ser Ala Trp Tyr Phe Asp Val Trp Gly Ala
            100                 105                 110 ggg acc acg gtc aca gtc                                              354
Gly Thr Thr Val Thr Val
            115
```

<210> SEQ ID NO 10
<211> LENGTH: 118
<212> TYPE: PRT
<213> ORGANISM: Mus musculus

<400> SEQUENCE: 10

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Trp Ile Gly Ser Ser Ala Trp Tyr Phe Asp Val Trp Gly Ala
            100                 105                 110

Gly Thr Thr Val Thr Val
            115
```

<210> SEQ ID NO 11
<211> LENGTH: 324
<212> TYPE: DNA
<213> ORGANISM: Mus musculus
<220> FEATURE:
<221> NAME/KEY: CDS
<222> LOCATION: (1)..(324)
<220> FEATURE:
<221> NAME/KEY: misc_feature
<222> LOCATION: (1)..(324)
<223> OTHER INFORMATION: Clone 19 Vk (polynucleotide and polypeptide
      sequences)

<400> SEQUENCE: 11

```
gaa aat gtg ctc acc cag tct cca gca atc atg tct gca tct cca ggg    48
Glu Asn Val Leu Thr Gln Ser Pro Ala Ile Met Ser Ala Ser Pro Gly
1               5                   10                  15 gaa aag gtc acc atg acc tgc agg gcc agc tca agt gta att tcc agt    96
Glu Lys Val Thr Met Thr Cys Arg Ala Ser Ser Ser Val Ile Ser Ser
            20                  25                  30 tac ttg cac tgg tac cag cag aag tca ggt gcc tcc ccc aaa ctc tgg   144
Tyr Leu His Trp Tyr Gln Gln Lys Ser Gly Ala Ser Pro Lys Leu Trp
        35                  40                  45 att tat agc act tcc aac ttg gct tct gga gtc cct gat cgc ttc agt   192
Ile Tyr Ser Thr Ser Asn Leu Ala Ser Gly Val Pro Asp Arg Phe Ser
    50                  55                  60 ggc agt ggg tct ggg acc tct tac tct ctc aca atc agc agt gtg gag   240
Gly Ser Gly Ser Gly Thr Ser Tyr Ser Leu Thr Ile Ser Ser Val Glu
65                  70                  75                  80 gct gaa gat gct gcc act tat tac tgc cag cag tac aat ggt tac ccg   288
Ala Glu Asp Ala Ala Thr Tyr Tyr Cys Gln Gln Tyr Asn Gly Tyr Pro
                85                  90                  95 ctc acg ttc ggt gct ggg acc aag ctg gaa ata aaa                   324
Leu Thr Phe Gly Ala Gly Thr Lys Leu Glu Ile Lys
            100                 105
```

<210> SEQ ID NO 12
<211> LENGTH: 108
<212> TYPE: PRT
<213> ORGANISM: Mus musculus

<400> SEQUENCE: 12

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Val Ile Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Asp Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asn Gly Tyr Pro
                85                  90                  95

Leu Thr Phe Gly Ala Gly Thr Lys Leu Glu Ile Lys
            100                 105
```

<210> SEQ ID NO 13
<211> LENGTH: 354
<212> TYPE: DNA
<213> ORGANISM: Mus musculus
<220> FEATURE:
<221> NAME/KEY: CDS
<222> LOCATION: (1)..(354)
<220> FEATURE:
<221> NAME/KEY: misc_feature
<222> LOCATION: (1)..(354)
<223> OTHER INFORMATION: Clone 19 VH (polynucleotide and polypeptide
      sequences)

<400> SEQUENCE: 13

```
cag gtt cag cta cag cag tct ggg gct gag ctg gtg aag cct ggg gcc     48
Gln Val Gln Leu Gln Gln Ser Gly Ala Glu Leu Val Lys Pro Gly Ala
1               5                   10                  15 tca gtg aag atg tcc tgc aag gct ttt ggc tac acc ttc act acc tat     96
Ser Val Lys Met Ser Cys Lys Ala Phe Gly Tyr Thr Phe Thr Thr Tyr
            20                  25                  30 cca ata gag tgg atg aag cag aat cat ggg aag agc cta gag tgg att    144
Pro Ile Glu Trp Met Lys Gln Asn His Gly Lys Ser Leu Glu Trp Ile
        35                  40                  45 gga aat ttt cat cct tac aat gat gat act aag tac aat gaa aaa ttc    192
Gly Asn Phe His Pro Tyr Asn Asp Asp Thr Lys Tyr Asn Glu Lys Phe
    50                  55                  60 aag ggc aag gcc aaa ttg act gta gaa aaa tcc tct acc aca gtc tac    240
Lys Gly Lys Ala Lys Leu Thr Val Glu Lys Ser Ser Thr Thr Val Tyr
65                  70                  75                  80 ttg gag ctc agc cga tta aca tct gac gac tct gct gtt tat tac tgt    288
Leu Glu Leu Ser Arg Leu Thr Ser Asp Asp Ser Ala Val Tyr Tyr Cys
                85                  90                  95 gca agg gag aac tac ggt agt cac ggg ggt ttt gtt tac tgg ggc caa    336
Ala Arg Glu Asn Tyr Gly Ser His Gly Gly Phe Val Tyr Trp Gly Gln
            100                 105                 110 ggg act ctg gtc acc gtc                                            354
Gly Thr Leu Val Thr Val
            115
```

```
<210> SEQ ID NO 14
<211> LENGTH: 118
<212> TYPE: PRT
<213> ORGANISM: Mus musculus

<400> SEQUENCE: 14

Gln Val Gln Leu Gln Gln Ser Gly Ala Glu Leu Val Lys Pro Gly Ala
1               5                   10                  15

Ser Val Lys Met Ser Cys Lys Ala Phe Gly Tyr Thr Phe Thr Thr Tyr
            20                  25                  30

Pro Ile Glu Trp Met Lys Gln Asn His Gly Lys Ser Leu Glu Trp Ile
        35                  40                  45

Gly Asn Phe His Pro Tyr Asn Asp Asp Thr Lys Tyr Asn Glu Lys Phe
    50                  55                  60

Lys Gly Lys Ala Lys Leu Thr Val Glu Lys Ser Ser Thr Thr Val Tyr
65                  70                  75                  80

Leu Glu Leu Ser Arg Leu Thr Ser Asp Asp Ser Ala Val Tyr Tyr Cys
                85                  90                  95

Ala Arg Glu Asn Tyr Gly Ser His Gly Phe Val Tyr Trp Gly Gln
            100                 105                 110

Gly Thr Leu Val Thr Val
        115

<210> SEQ ID NO 15
<211> LENGTH: 15
<212> TYPE: PRT
<213> ORGANISM: Artificial Sequence
<220> FEATURE:
<223> OTHER INFORMATION: Clone 2 Vk CDR1

<400> SEQUENCE: 15

Arg Ala Ser Lys Ser Val Ser Thr Ser Gly Phe Asn Tyr Ile His
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Clone 2 Vk CDR2

<400> SEQUENCE: 16

Leu Ala Ser Asn Leu Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Clone 2 Vk CDR3

<400> SEQUENCE: 17

Gln His Ser Arg Glu Leu Pro Leu Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Clone 2 VH CDR1
```

<400> SEQUENCE: 18

Gly Tyr Thr Phe Thr Thr Tyr Tyr Leu Tyr
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Clone 2 VH CDR2

<400> SEQUENCE: 19

Gly Ile Asn Pro Ser Asn Gly Gly Thr Asn Phe Asn Glu Lys Phe Lys
1               5                   10                  15

Ser

<210> SEQ ID NO 20
<211> LENGTH: 11
<212> TYPE: PRT
<213> ORGANISM: Artificial Sequence
<220> FEATURE:
<223> OTHER INFORMATION: Clone 2 VH CDR3

<400> SEQUENCE: 20

Arg Asp Tyr Arg Tyr Asp Arg Gly Phe Asp Tyr
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Clone 10 VK CDR1

<400> SEQUENCE: 21

Arg Ser Gly Gln Asn Ile Val His Ser Asn Gly Asn Thr Tyr Leu Glu
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Clone 10 Vk CDR2

<400> SEQUENCE: 22

Lys Val Ser Asn Arg Phe Phe
1               5

<210> SEQ ID NO 23
<211> LENGTH: 9
<212> TYPE: PRT
<213> ORGANISM: Artificial Sequence
<220> FEATURE:
<223> OTHER INFORMATION: Clone 10 Vk CDR3

<400> SEQUENCE: 23

Phe Gln Gly Ser His Val Pro Phe Thr
1               5

<210> SEQ ID NO 24
<211> LENGTH: 11
<212> TYPE: PRT

<213> ORGANISM: Artificial Sequence
<220> FEATURE:
<223> OTHER INFORMATION: Clone 10 VH

<400> SEQUENCE: 24

Gly Tyr Ser Ile Thr Ser Asp Tyr Ala Trp Asn
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Clone 10 VH CDR2

<400> SEQUENCE: 25

Tyr Ile Asn Tyr Ser Gly Ser Thr Ser Tyr Asn Pro Ser Leu Lys Ser
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Clone 10 VH

<400> SEQUENCE: 26

Trp Ile Gly Ser Ser Ala Trp Tyr Phe Asp Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Clone 19 Vk CDR1

<400> SEQUENCE: 27

Arg Ala Ser Ser Ser Val Ile Ser Ser Tyr Leu His
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Clone 19 Vk CDR2

<400> SEQUENCE: 28

Ser Thr Ser Asn Leu Ala Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Clone 19 Vk CDR3

<400> SEQUENCE: 29

Gln Gln Tyr Asn Gly Tyr Pro Leu Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Clone 19 VH CDR1

<400> SEQUENCE: 30

Gly Tyr Thr Phe Thr Thr Tyr Pro Ile Glu
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Clone 19 VH CDR2

<400> SEQUENCE: 31

Asn Phe His Pro Tyr Asn Asp Asp Thr Lys Tyr Asn Glu Lys Phe Lys
1               5                   10                  15

Gly

<210> SEQ ID NO 32
<211> LENGTH: 11
<212> TYPE: PRT
<213> ORGANISM: Artificial Sequence
<220> FEATURE:
<223> OTHER INFORMATION: Clone 19 VH CDR3

<400> SEQUENCE: 32

Glu Asn Tyr Gly Ser His Gly Gly Phe Val Tyr
1               5                   10

<210> SEQ ID NO 33
<211> LENGTH: 51
<212> TYPE: DNA
<213> ORGANISM: Artificial Sequence
<220> FEATURE:
<223> OTHER INFORMATION: oligonucleotide 1 primer

<400> SEQUENCE: 33
tagtagagat ctctcaagca ggccaccatg caaatcccac aggcgccgtg g                51

<210> SEQ ID NO 34
<211> LENGTH: 47
<212> TYPE: DNA
<213> ORGANISM: Artificial Sequence
<220> FEATURE:
<223> OTHER INFORMATION: oligonucleotide 2 primer

<400> SEQUENCE: 34
tcagccggat ccttccaaac cctggtgctc tgctacttgc tagatgg                     47

<210> SEQ ID NO 35
<211> LENGTH: 39
<212> TYPE: DNA
<213> ORGANISM: Artificial Sequence
<220> FEATURE:
<223> OTHER INFORMATION: oligonucleotide 3 primer

<400> SEQUENCE: 35
atcacagccc tgtacctgaa tagtagaagg aatagactc                              39

<210> SEQ ID NO 36
<211> LENGTH: 30
<212> TYPE: DNA
<213> ORGANISM: Artificial Sequence
<220> FEATURE:
<223> OTHER INFORMATION: oligonucleotide 4 primer

```
<400> SEQUENCE: 36
ctcgagctac tagggcggt acgctgcaaa                              30

<210> SEQ ID NO 37
<211> LENGTH: 47
<212> TYPE: DNA
<213> ORGANISM: Artificial Sequence
<220> FEATURE:
<223> OTHER INFORMATION: oligonucleotide 2 primer

<400> SEQUENCE: 37
gcccagccgg ccagttccaa acctttggg tgctggtggt ggttggt           47

<210> SEQ ID NO 38
<211> LENGTH: 36
<212> TYPE: DNA
<213> ORGANISM: Artificial Sequence
<220> FEATURE:
<223> OTHER INFORMATION: oligonucleotide 3 primer

<400> SEQUENCE: 38
tttgcagcgt accgcccac gcgttagtag ctcgag                       36
```

PD-1 SPECIFIC ANTIBODIES AND USES THEREOF

CROSS-REFERENCE TO RELATED APPLICATIONS

This application is the U.S. national stage application of International Patent Application No. PCT/IB2009/006946, filed Sep. 14, 2009, which claims the benefit of U.S. Provisional Patent Application No. 61/096,485, filed Sep. 12, 2008, the disclosures of which are hereby incorporated by reference in their entireties, including all figures, tables and amino acid or nucleic acid sequences.

The Sequence Listing for this application is labeled "SeqList.txt" which was created on Sep. 10, 2009 and is 26 KB. The entire contents of the sequence listing is incorporated herein by reference in its entirety.

SUMMARY OF THE INVENTION

One aspect of the present disclosure provides antibodies that can act as agonists of PD-1, thereby modulating immune responses regulated by PD-1. In one embodiment, the anti-PD-1 antibodies can be novel antigen-binding fragments. Anti-PD-1 antibodies disclosed herein are able to bind to human PD-1 and agonize the activity of PD-1, thereby inhibiting the function of immune cells expressing PD-1. Exemplary antibodies for use in the context of this disclosure include, but are not limited to monoclonal antibody produced by clone 10.

Another aspect of the disclosure provides compositions comprising PD-1 specific antibodies and their use in methods of down regulating the immune response. These methods can be practiced on any subject, including humans or animals. In particular embodiments, anti-PD-1 antibodies are used to treat or prevent immune disorders by reducing the T cell response. Non-limiting examples of immune disorders that can be treated via the administration of PD-1 specific antibodies to a subject include, but are not limited to, rheumatoid arthritis, multiple sclerosis, inflammatory bowel disease, Crohn's disease, systemic lupus erythematosus, type I diabetes, transplant rejection, graft-versus-host disease, hyperproliferative immune disorders, cancer, and infectious diseases. Some embodiments of this aspect of the invention may use two PD-1 specific antibodies that bind to distinct, non-overlapping epitopes.

Anti-PD-1 antibodies disclosed herein may be used, in another aspect of the invention to detect PD-1 or its fragments in a biological sample. The amount of PD-1 detected may be correlated with the expression level of PD-1, and associated with the activation status of immune cells (e.g., activated T cells, B cells, and/or monocytes) in the subject.

BRIEF DESCRIPTION OF THE FIGURES

(FIG. 4A) A chimera consisting of the extracellular region of human PD-1 and the transmembrane and cytoplasmic regions of mouse (m) TCRζ and CD28 was expressed in DO11.10 cells. (FIG. 4B) The cells were treated with immobilized anti-CD3 (KT3) or anti-PD-1 antibodies and the amount of IL-2 released was measured.

Figures 10A, 10B:
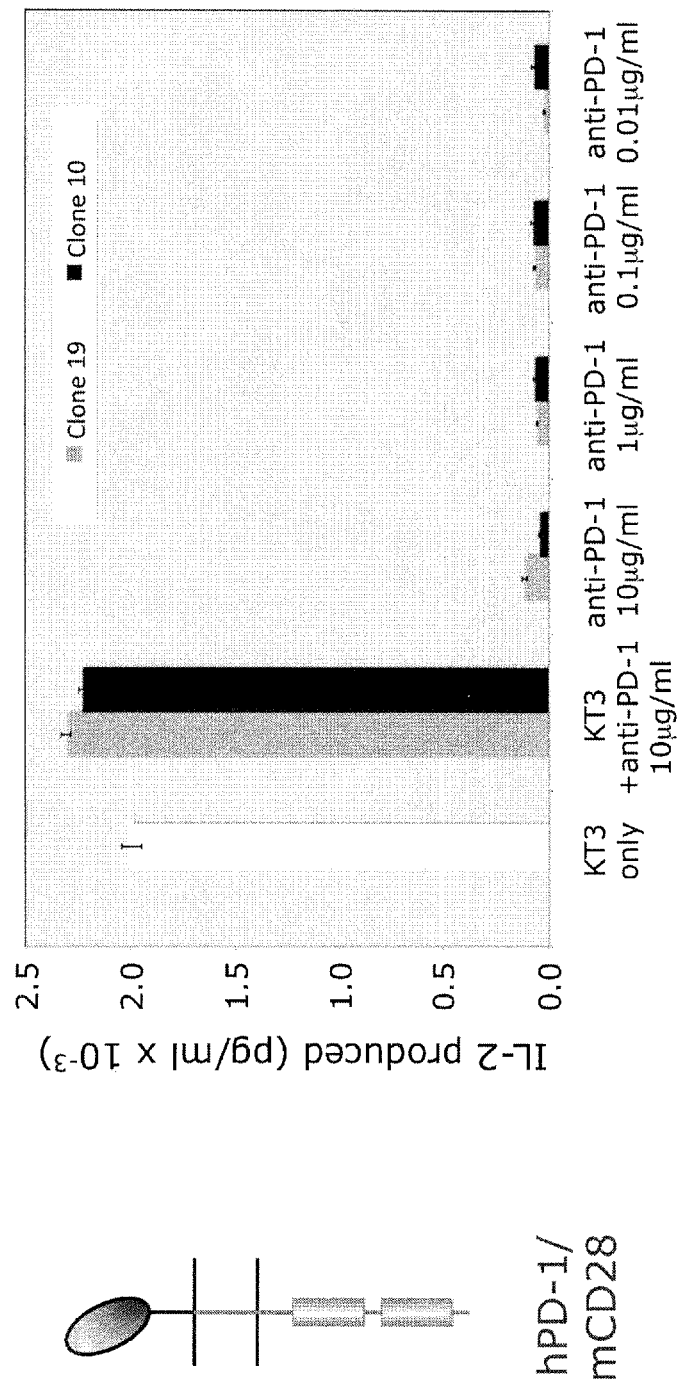

FIGS. 10A-10B: IL-2 secretion induced by anti-PD-1 antibodies binding to a hPD-1/mCD28 chimera. (FIG. 10A) A chimera consisting of the extracellular region of human PD-1 and the transmembrane and cytoplasmic regions of mouse CD28 was expressed in DO11.10 cells. (FIG. 10B) The cells were treated with immobilized anti-CD3 (KT3) or anti-PD-1 antibodies and the amount of IL-2 released was measured.

FIGS. 11A-11C: Strong signaling induced by a pair of antibodies binding to a monomeric signaling protein. (FIG. 11A) Antibodies, which are bivalent, cause strong signaling by homodimeric receptors because they are able to generate a high local density of signaling domains. (FIG. 11B) In contrast, antibodies are only able to recruit pairs of monomeric receptors, such as PD-1, leading to much less intense signaling. (FIG. 11C) By using antibodies that bind to two non-overlapping epitopes, higher densities of monomeric signaling receptors can be generated, giving much more potent signaling.

Figure 12:
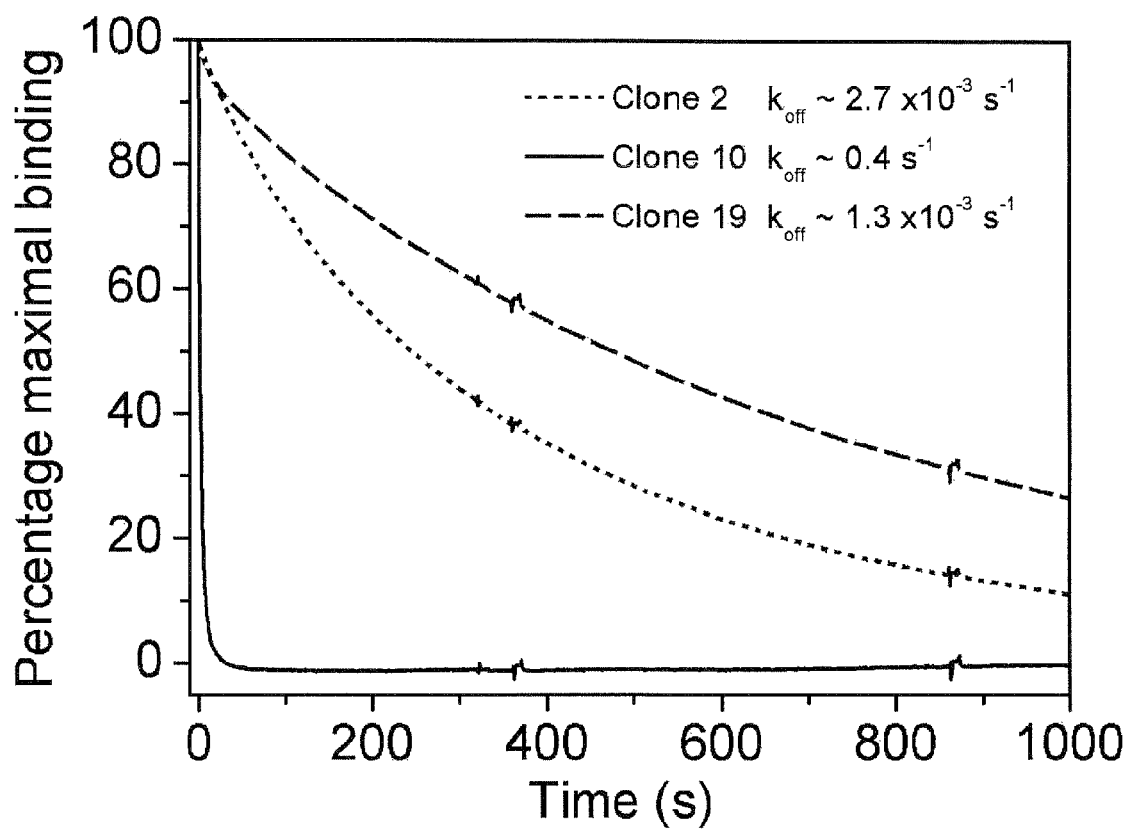

FIG. 12: Dissociation rates for Clone 2, 10 and 19 antibodies determined by surface plasmon resonance-based analysis. The three antibodies and a negative control (OX-7) were bound indirectly to the biosensor surface, i.e. via a covalently coupled rabbit anti-mouse Fc antibody. Monomeric soluble human PD-1 was then injected to saturating levels over the immobilized antibodies in the buffer 10 mM Hepes, 150 mM NaCl pH 7.4. Following injection of the soluble PD-1, the buffer only was injected, allowing dissociation of the bound soluble PD-1 from each of the antibodies simultaneously. Dissociation rates were fitted using Origin v.5.0 software (MicroCal Software Inc, Northampton, Mass.) after subtraction of the dissociation rate for OX-7 dissociating from the anti-mouse Fc antibody.

Figure 13:
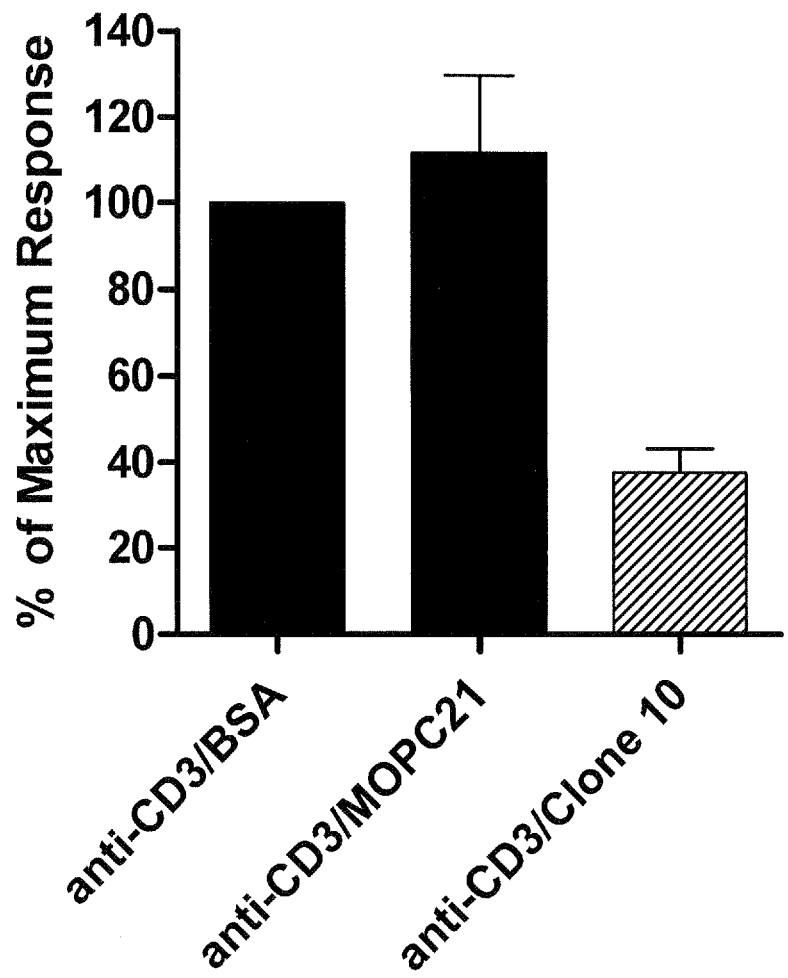

FIG. 13: Inhibition of CD4$^+$ T cell proliferation by anti-PD-1 antibodies. CD4$^+$ T cells were purified from human PBL by negative selection and cultured with Dynalbeads coated with anti-CD3 plus control (BSA or MOPC21) or Clone 10 antibody. Proliferation (y-axis) was measured by $^3$H-thymidine incorporation at day 6. Bars represent the % of maximal response (anti-CD3/BSA) and are the mean+/−S.E.M. of 4 different donor cultures.

DETAILED DESCRIPTION

The term "antibody", as used in this disclosure, refers to an immunoglobulin or a fragment or a derivative thereof, and encompasses any polypeptide comprising an antigen-binding site, regardless of whether it is produced in vitro or in vivo. Thus, an antibody includes, but is not limited to, polyclonal, monoclonal, monospecific, polyspecific, bispecific, humanized, single-chain, chimeric, synthetic, recombinant, hybrid, mutated, and grafted antibodies.

The term "antibody fragment" or "an antigen binding fragment" includes antibody fragments such as Fab, F(ab')$_2$, Fv, scFv, Ed, dab, and other antibody fragments that retain antigen-binding function, i.e., the ability to bind PD-1 specifically and/or that are produced from a monoclonal antibody disclosed herein. These fragments comprise an antigen-binding domain and can also, in some embodiments, agonize the function of PD-1. Antibodies disclosed herein, and fragments thereof, include those antibodies having altered glycosylation patterns when compared to the parent antibody (e.g., the antibody produced by clone 10 and/or clone 19).

As discussed above, the PD-1 antibodies disclosed herein are able to antagonize the activity and/or proliferation of lymphocytes by agonizing PD-1. The term "antagonize the activity" relates to a decrease (or reduction) in lymphocyte proliferation or activity that is at least about 10%, 20%, 30%, 40%, 50%, 60%, 70%, 80%, 90%, or more. The term "antagonize" may be used interchangeably with the terms "inhibitory" and "inhibit". PD-1-mediated activity can be determined quantitatively using T cell proliferation assays as described herein.

The terms "therapeutically effective", "therapeutically effective amount", "effective amount" or "in an amount effective" refers to a dosage or amount of the disclosed antibodies that is sufficient to agonize the activity of PD-1 and provide for the amelioration of symptoms in a subject or to achieve a desired biological response, e.g., decreased T cell activity, etc.

The term "isolated" refers to a molecule that is substantially free of its natural environment. For instance, an isolated antibody is substantially free of cellular material or other proteins from the cell (e.g., hybridoma) or other source from which it is derived. The term isolated also refers to preparations where the isolated protein is sufficiently pure to be administered as a pharmaceutical composition, or at least 70-80% (w/w) pure, at least 80-90% (w/w) pure, 90-95% pure; or at least 95%, 96%, 97%, 98%, 99%, or 100% (w/w) pure.

One aspect of the present disclosure provides antibodies that can act as agonists of PD-1, thereby modulating immune responses regulated by PD-1. In one embodiment, the anti-PD-1 antibodies can be novel antigen-binding fragments. Anti-PD-1 antibodies disclosed herein are able to bind to including human PD-1 and agonize PD-1, thereby inhibiting the function of immune cells expressing PD-1. In some embodiments, the immune cells are activated lymphocytes, such as T-cells, B-cells and/or monocytes expressing PD-1. Exemplary antibodies for use in the context of this disclosure include, but are not limited to monoclonal antibodies produced by clone 10. Some embodiments of this aspect of the invention may use two PD-1 specific antibodies that bind to distinct, non-overlapping epitopes. Other embodiments provide for antibodies that compete with one another for binding to an epitope present on PD-1 (e.g., Clone 10 and Clone 2).

Anti-PD1 antibodies described herein can be linked to another molecule/moiety. Non-limiting examples include another peptide or protein (albumin, another antibody, etc.), toxins, radioisotopes, cytotoxic agents or cytostatic agents. The term "link" or "linked" relates to the chemical cross-linking or covalent attachment of another molecule/moiety by recombinant methods. Antibodies disclosed herein may also be linked to one or more nonproteinaceous polymers, e.g., polyethylene glycol, polypropylene glycol, or polyoxyalkylenes (see, for example, U.S. Pat. Nos. 4,791,192; 4,766,106; 4,670,417; 4,640,835; 4,609,546; 4,496,689; 4,495,285; 4,301,144; and 4,179,337, which are each hereby incorporated by reference in their entireties).

The antibodies may also be tagged with a detectable, or functional, label. Detectable labels include radiolabels such as $^{99}$Tc, which may also be attached to antibodies using conventional chemistry. Detectable labels also include enzyme labels such as horseradish peroxidase or alkaline phosphatase. Other types of detectable labels include chemical moieties such as biotin, which may be detected via binding to a specific cognate detectable moiety, e.g., labeled avidin.

Another aspect of the invention provides for the use of antibodies disclosed herein for isolating PD-1 or PD-1-expressing cells. Yet another aspect of the invention provides methods of inducing tolerance to a specific antigen. For example, tolerance can be induced by co-administration of antigen and an anti-PD-1 antibody disclosed herein. Still other aspects of the invention relate to reducing immune responses mediated by activated lymphocytes in a subject comprising the administration of anti-PD-1 antibodies disclosed herein. Another aspect of the invention provides for the use of the disclosed anti-PD-1 antibodies for agonizing PD-1 and down regulating immune responses (or in some cases inhibiting or reducing the proliferation of activated lymphocytes). In particular embodiments, the immune response is TcR/CD28-mediated. As discussed herein, allergies, rheumatoid arthritis, type I diabetes mellitus, multiple sclerosis, inflammatory bowel disease, Crohn's disease, systemic lupus erythematosus, tissue, skin and organ transplant rejection or graft-versus-host disease (GVHD) can be treated via the administration of anti-PD-1 antibodies. Some embodiments of this aspect of the invention may use two PD-1 specific antibodies that bind to distinct, non-overlapping epitopes.

Another aspect of the disclosure provides compositions comprising PD-1 specific antibodies and their use in methods of down regulating the immune response (or reducing the proliferation of activated T-cells, B-cells or mononuclear cells). These methods can be practiced on any subject, including humans or animals. In particular embodiments, anti-PD-1 antibodies are used to treat or prevent immune disorders by reducing the T cell response. Non-limiting examples of immune disorders that can be treated via the administration of PD-1 specific antibodies to a subject include, but are not limited to, rheumatoid arthritis, multiple sclerosis, inflammatory bowel disease, Crohn's disease, systemic lupus erythematosus, type I diabetes, transplant rejection, graft-versus-host disease, hyperproliferative immune disorders, cancer, and infectious diseases. Yet other aspects of the invention provide for inhibiting or reducing lymphocyte (T-cell, B-cell and/or monocyte) activity in inflammatory lesions. Some embodiments of this aspect of the invention may use two PD-1 specific antibodies that bind to distinct, non-overlapping epitopes (such antibodies can be affinity matched to provide a desired activity in vivo (e.g., Clone 19 and Clone 2)).

As illustrated in FIG. 12, the antibody produced by clone 10 has a relatively low affinity for PD-1. Such low affinity antibodies can be used in a manner similar to ligands of PD-1. For example, the Clone 10 antibody has a very fast off-rate (similar to that for one of the native ligands for PD-1 (i.e., PD-L2)). A fast off-rate gives good signaling by Clone 10 in vitro because it may allow for the "serial engagement" of multiple PD-1 molecules. Thus, antibodies such as those produced by clone 10 can be used to engage numerous PD-1 molecules and cause inhibitory signaling.

Anti-PD-1 antibodies disclosed herein may be used, in another aspect of the invention to detect PD-1 or its fragments in a biological sample. The amount of PD-1 detected may be correlated with the expression level of PD-1, and associated with the activation status of immune cells (e.g., activated T cells, B cells, and/or monocytes) in the subject.

Another aspect of the invention provides anti-PD-1 specific monoclonal antibodies having modified binding affinity. One embodiment provides for modifying the binding affinity such that the antibody has a low affinity for PD-1 (e.g., the antibody has a dissociation rate of between 0.1 $sec^{-1}$ and 0.5 $sec^{-1}$ or less than 0.90 $sec^{-1}$). Particular embodiments provided antibodies having off rates of 0.10 $sec^{-1}$, 0.15 $sec^{-1}$, 0.20 $sec^{-1}$, 0.25 $sec^{-1}$, 0.30 $sec^{-1}$, 0.35 $sec^{-1}$, 0.40 $sec^{-1}$, 0.45 $sec^{-1}$ or 0.50 $sec^{-1}$ or for antibodies having dissociation rates ranging from 0.04 $sec^{-1}$ to 2.0 $sec^{-1}$ (e.g., 0.04 $sec^{-1}$, 0.05 $sec^{-1}$, 0.06 $sec^{-1}$, 0.07 $sec^{-1}$, 0.08 $sec^{-1}$, 0.09 $sec^{-1}$, 0.10 $sec^{-1}$, 0.15 $sec^{-1}$, 0.20 $sec^{-1}$, 0.25 $sec^{-1}$, 0.30 $sec^{-1}$, 0.35 $sec^{-1}$, 0.40 $sec^{-1}$, 0.45 $sec^{-1}$, 0.50 $sec^{-1}$, 0.55 $sec^{-1}$, 0.60 $sec^{-1}$, 0.65 $sec^{-1}$, 0.70 $sec^{-1}$, 0.75 $sec^{-1}$, 0.80 $sec^{-1}$, 0.85 $sec^{-1}$, 0.90 $sec^{-1}$, 0.95 $sec^{-1}$, 1.0 $sec^{-1}$, 1.10 $sec^{-1}$, 1.20 $sec^{-1}$, 1.30 $sec^{-1}$, 1.40 $sec^{-1}$, 1.50 $sec^{-1}$, 1.60 $sec^{-1}$, 1.70 $sec^{-1}$, 1.80 $sec^{-1}$, 1.90 $sec^{-1}$, or 2.00 $sec^{-1}$). Antibodies having such binding affinities can be modified in any suitable process.

Thus, the binding affinity of the antibodies (such as those produced by clone 2, clone 10 or clone 19) can be increased or decreased via various methods known in the art. For example, binding characteristics can be modified by direct mutation, methods of affinity maturation, phage display, or chain shuffling within the nucleic acids encoding the antibody molecules. Individual residues or combinations of residues can be randomized so that in a population of otherwise identical antigen binding sites, all twenty amino acids are found at particular positions and binding characteristics/affinities can also be modified by methods of affinity maturation. (See, e.g., Yang et al. (1995) *J. Mol. Biol.* 254, 392-403; Hawkins et al. (1992) *J. Mol. Bio.* 226, 889-896; or Low et al. (1996) *J. Mol. Biol.* 250, 359-368 (each of which is hereby incorporated by reference in its entirety, particularly with respect to methods of increasing or decreasing the binding affinity of antibodies)). Methods known in the art include, for example, Marks et al. *BioTechnology*, 10, 779-783 (1992), which describes affinity maturation by VH and VL domain shuffling; random mutagenesis of CDR and/or framework residues is described by: Barbas et al. *Proc Nat. Acad. Sci, USA* 91, 3809-3813 (1994); Schier et al. *Gene*, 169, 147-155 (1995); Yelton et al. *J Immunol.*, 155, 1994-2004 (1995); Jackson et al. *J. Immunol.*, 154, 3310-9 (1995); and Hawkins et al. *J. Mol. Biol.*, 226, 889-896 (1992).

Strategies for antibody optimization are sometimes carried out using random mutagenesis. In these cases positions are chosen randomly, or amino acid changes are made using simplistic rules. For example all residues may be mutated to alanine, referred to as alanine-scanning. WO 9523813 (which is hereby incorporated by reference in its entirety) teaches in vitro methods of altering antibody affinities utilizing alanine-scanning mutagenesis. Alanine-scanning mutagenesis can also be used, for example, to map the antigen binding residues of an antibody (Kelley et al. *Biochemistry* 32, 6828-6835 (1993); Vajdos et al. *J. Mol. Biol.* 320, 415-428 (2002)). Sequence-based methods of affinity maturation (see, U.S. Pat. Application No. 2003/022240A1 and U.S. Pat. No. 2002/177170A1, both hereby incorporated by reference in their entireties) may also be used to increase or decrease the binding affinities of antibodies. Finally, the binding affinities of antibodies in which the binding affinity has been altered can be determined using methods as disclosed herein (for example, dissociation rates for modified antibodies can be determined by surface plasmon resonance-based analysis as described for FIG. 12). T cells can be activated by any T-cell activating compound. As discussed in the examples, one such T-cell-activating compound is an anti-CD3 antibody, which binds TcR. Activating anti-CD3 antibodies are known in the art (see, for example, U.S. Pat. Nos. 6,405,696 and 5,316,763 [each of which is hereby incorporated by reference in its entirety]). The ratio between the activating TcR signal and negative PD-1 signal is determined experimentally using conventional procedures known in the art or as described in the Examples.

The antibodies or antibody compositions of the present invention are administered in therapeutically effective amounts. Generally, a therapeutically effective amount may vary with the subject's age, condition, and sex, as well as the severity of the medical condition of the subject. A therapeutically effective amount of antibody ranges from about 0.001 to about 25 mg/kg body weight, preferably from about 0.01 to about 25 mg/kg body weight, from about 0.1 to about 20 mg/kg body weight, or from about 1 to about 10 mg/kg. The dosage may be adjusted, as necessary, to suit observed effects of the treatment. The appropriate dose is chosen based on clinical indications by a treating physician.

In another aspect, the antibodies of the invention can be used as a targeting agent for delivery of another therapeutic or a cytotoxic agent (e.g., a toxin) to a cell expressing PD-1. The method includes administering an anti-PD-1 antibody coupled to a therapeutic or a cytotoxic agent or under conditions that allow binding of the antibody to PD-1 expressed on the cell surface.

Still other aspects of the invention provide for the use of the disclosed antibodies for detecting the presence of PD-1 in biological samples. The amount of PD-1 detected may be correlated with the expression level of PD-1, which, in turn, is correlated with the activation status of immune cells (e.g., activated T cells, B cells, and monocytes) in the subject.

The subject invention also provides methods of binding an antibody to a PD-1 polypeptide comprising contacting a sample that may contain PD-1 or cells expressing PD-1 with an antibody under conditions that allow for the formation of an antibody-antigen complex. These methods can further comprise the step of detecting the formation of said antibody-antigen complex. The complex can be detected using any means known in the art (e.g., fluorescence activated cell sorting, radioimmunoassays, or chromogenic assays).

Another aspect of the disclosure provides compositions comprising anti-PD-1 antibodies. These compositions can be formulated according to known methods for preparing pharmaceutically useful compositions. Formulations are described in a number of sources which are well known and readily available to those skilled in the art. For example, *Remington's Pharmaceutical Science* (Martin E. W., Easton Pa., Mack Publishing Company, 19$^{th}$ ed., 1995) describes formulations which can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Another aspect of the invention provides nucleic acids encoding PD-1 specific antibodies disclosed herein. For example, the nucleic acids encoding the antibody secreted by clone 10 or clone 2 can be isolated according to methods known to those skilled in the art. Yet another aspect of the invention provides vectors and transformed host cells comprising a nucleic acid encoding a PD-1 specific antibody as secreted by clone 10 or clone 2. As would be apparent to those skilled in the art, constant regions of the murine antibodies disclosed herein can be substituted with human constant regions to form chimeric antibodies comprising murine variable regions and human constant regions. Some embodiments provide for the substitution of heavy chain constant regions on the disclosed antibodies that provide for higher Fc receptor binding by the antibodies (e.g., human IgG1, IgG3, and murine IgG2a isotypes, all of which bind Fc receptors strongly, can be grafted onto variable regions of the disclosed antibodies without affecting binding specificity). Alternatively, CDRs from the murine antibodies disclosed herein can be isolated and grafted into human framework regions to form humanized antibodies. Finally, methods of producing the disclosed PD-1 specific antibodies (including methods of producing the aforementioned humanized and chimeric antibodies) are also provided by the subject invention.

The hybridomas disclosed herein were deposited on Sep. 9, 2008 with European Collection of Cell Cultures (ECACC), Centre For Emergency Preparedness and Response, The Health Protection Agency, Porton Down, Salisbury, Wiltshire, SP4 0JG United Kingdom. The accession numbers for the hybridomas are as follows:

Clone 2: 08090903;
Clone 10: 08090902; and
Clone 19: 08090901.

As discussed above, antibodies disclosed herein can be a full-length murine, human, humanized, or chimeric antibody; or a fragment or derivative thereof. In one embodiment, the antibody binds the same, or substantially the same, epitope as clone 10 or clone 2 or by a monoclonal antibody comprising: a) SEQ ID NO: 10 and SEQ ID NO: 8; or b) SEQ ID NO: 6 and SEQ ID NO: 2. In another embodiment, the antibody, including a fragment or derivative thereof, comprises the same or substantially identical VH and/or Vk regions as clone 10 (SEQ ID NOs: 10 and 8) or clone 2 (SEQ ID NOs: 6 and 2).

In another embodiment, the antibody, including a fragment or derivative thereof, comprises the same or substantially identical CDR1, CDR2 and CDR3 regions as those found in the Vk and VH sequences of clone 10 or clone 2. In one embodiment, the antibody comprises: a) SEQ ID NO: 10 and SEQ ID NO: 8; or b) SEQ ID NO: 6 and SEQ ID NO: 2, as well as the sequence for murine IgG1 constant heavy chain region (GenBank accession No. D78344, hereby incorporated by reference in its entirety) and the sequence for murine IgG1 constant light chain region (GenBank accession No. V00807, hereby specifically incorporated by reference in its entirety). Other aspects of the invention provide nucleotide sequences encoding the disclosed antibodies, expression vectors comprising such sequences, host cells comprising such vectors, and methods of producing such antibodies from such host cells.

Fragments and derivatives of antibodies of this invention can be produced by techniques that are known in the art. "Immunoreactive fragments" comprise a portion of the intact antibody, generally the antigen binding site or variable region. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. For instance, Fab or F(ab')$_2$ fragments may be produced by protease digestion of the isolated antibodies, according to conventional techniques. Alternatively, the DNA of a hybridoma producing an antibody of this invention may be modified so as to encode for a fragment of this invention. The modified DNA is then inserted into an expression vector and used to transform or transfect an appropriate cell, which then expresses the desired fragment.

In an alternate embodiment, the DNA of a hybridoma producing an antibody of this invention can be modified prior to insertion into an expression vector, for example, by substituting the coding sequence for human heavy- and light-chain constant domains in place of the homologous non-human sequences (e.g., Morrison et al., Proc. Natl. Acad. Sci. U.S.A., 81, pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention. Thus, the antibodies of the present invention may also be made into "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. U.S.A., 81, pp. 6851 (1984)).

In an exemplary embodiment, a chimeric recombinant mAb from clone 10 or clone 2 VH and Vk sequences, or a derivative or variant thereof, is produced. Nucleic acid sequences encoding the clone 10 or clone 2 VH and Vk sequences (SEQ ID NOs: 10 and 8 or SEQ ID NOs: 6 and 2, respectively) are cloned into a commercially available or otherwise known eukaryotic expression vector containing the light and heavy chain constant regions for a human or non-human antibody, using standard techniques. One example of a commercially available vector is pASK84, available from the ATCC (American Type Culture Collection, catalog number 87094). CHO cells, or other mammalian cell lines are then transfected with the vectors by standard methods, as described for example in "Molecular Cloning", Sambrook et al. The result is transfected cell lines that stably express and secrete the antibody molecule of interest, such as a chimeric version of clone 10 or clone 2 comprising its original VH and Vk regions and the constant regions from a human mAb. The entire cDNA sequences encoding the constant regions of human IgG can be found in the following GenBank entries, each of which incorporated by reference in its entirety: Human IgG1 constant heavy chain region: GenBank accession #: J00228; Human IgG2 constant heavy chain region: GenBank accession #: J00230; Human IgG3 constant heavy chain region: GenBank accession #: X04646; Human IgG4 constant heavy chain region: GenBank accession #: K01316; and Human kappa light chain constant region: GenBank accession #: J00241.

Alternatively, VH and Vk regions of clone 10 or clone 2, or mutants or derivatives thereof, can be cloned into vectors encoding truncated constant regions in order to express antibody fragments (e.g., Fab fragments). Isotype-switching of antibody can be made according to similar principles. For example, an antibody with the exact same specificity as clone 10 or clone 2 but with a different isotype can be obtained by sub-cloning the cDNA encoding Vk and VH sequences into plasmids containing cDNA encoding human kappa light chain constant regions and a human heavy constant chain region selected from IgG1 or IgG2 or IgG3 or IgG4 constant heavy chain regions. Thus, an antibody as generated can possess any isotype and the antibody can then be isotype switched using conventional techniques in the art. Such techniques include the use of direct recombinant techniques (see, e.g., U.S. Pat. No. 4,816,397), cell-cell fusion techniques (see e.g., U.S. Pat. No. 5,916,771), and other suitable techniques known in the art. Accordingly, the effector function of antibodies provided by the invention may be "changed" with respect to the isotype of a parent antibody by isotype switching to, e.g., an IgG1, IgG2, IgG3, IgG4, IgD, IgA, IgE, or IgM antibody for various therapeutic or other uses.

According to another embodiment, the antibody of this invention is humanized. "Humanized" forms of antibodies according to this invention are specific chimeric immunoglobulins, immunoglobulin chains or fragments thereof (such as Fv, Fab, Fab', F(ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fe), typically that of a human immunoglobulin. For further details see Jones et al., Nature, 321, pp. 522 (1986); Reichmann et al., Nature, 332, pp. 323 (1988); and Presta, Curr. Op. Struct. Biol., 2, pp. 593 (1992). Accordingly, humanized versions of clone 10 or clone 2 antibodies comprising the VH and Vk CDR regions of clone 10 or clone 2 and constant and framework regions from a human mAb can be made, using known constant and framework human mAb sequences and established techniques in the art, as described herein. For any humanized antibody incorporating the clone 2 VH CDR1 domain, the domain can contain SEQ ID NO: 18 or amino acids 6-10 of SEQ ID NO: 18. For any humanized antibody incorporating the clone 10 VH CDR1 domain, the domain can contain SEQ ID NO: 24 or amino acids 6-11 of SEQ ID NO: 24.

Methods for humanizing the antibodies of this invention are well known in the art. Generally, a humanized antibody according to the present invention has one or more amino acid residues introduced into it from the original antibody. These murine or other non-human amino acid residues are often referred to as "import" residues, which are typically taken from an "import" variable domain. Humanization can be essentially performed following the method of Winter and co-workers (Jones et al., Nature, 321, pp. 522 (1986); Riechmann et al., Nature, 332, pp. 323 (1988); Verhoeyen et al., Science, 239, pp. 1534 (1988)). Accordingly, such "humanized" antibodies are chimeric antibodies (Cabilly et al., U.S. Pat. No. 4,816,567), wherein substantially less than an intact human variable domain has been substituted by the corresponding sequence from the original antibody. In practice, humanized antibodies according to this invention are typically human antibodies in which some CDR residues and possibly some FR residues are substituted by residues from analogous sites in the original antibody.

EXAMPLES

Example 1

Methods for Generation of Anti-PD-1 Antibodies 1.1 Myeloma Cell Line

For fusion the myeloma cell line SP2/0-Ag14 from the German Collection of Microorganisms and Cell Cultures (DSMZ GmbH, Braunschweig) was used. This cell line is a hybrid between BALB/c spleen cells and the myeloma cell line P3x63Ag8. The cells have been described as not synthesizing or secreting immunoglobulin chains, being resistant to 8-azaguanine at 20 µg/ml, and not growing in HAT (Hypoxanthine, Aminopterin, Thymidine) medium. The SP2/0 cells are routinely maintained in tissue culture flasks in standard growth medium (with 10% FCS). A new aliquot of frozen SP2/0 cells was used after a period of 2 weeks in order to avoid the implementation of HGPRT-positive revertants. The myeloma cells were shown to be negative in all mycoplasma tests.

1.2 Antigens for Immunization and Screening

The recombinant protein PD-1Fc was prepared using the methods described for the production of CD28Fc (Evans et al. Nat Immunol. 6, 271-9 (2005)) and concentrated to 5.1 mg/ml in 0.01 M HEPES, 150 mM NaCl, pH 7.4. SDS-PAGE analysis of the antigen run under reducing and non-reducing conditions established the purity of the protein to be >95%.

1.3 Immunization

Five mice (about 8 weeks old) were immunized via the intraperitoneal cavity using an immunization protocol over 60 days. For immunization an alum precipitate of the immunogen was prepared. The alum precipitate was freshly prepared for each boost. The mice were immunized with 50 µg protein and boosted with 25 µg protein. Three mice were used for fusion.

1.4 General Handling of Cells

Cells were handled under sterile conditions using a laminar air-flow system, sterile materials and sterile solutions. Cells were incubated at 37° C. in a humid atmosphere containing 5% carbon dioxide. For cultivation of the hybridoma cells a complete growth medium (CGM) containing DMEM with supplements 2-mercaptoethanol, L-Glutamine, GlutaMax, HT, non essential amino acids, sodium pyruvate, antibiotics/antimycotic solution (in concentrations recommended by the supplier) and FCS at different concentrations (10%, 15% or 20%) was used.

1.5 Preparation of Spleen Cells and Cell Fusions

After asphyxiation of the three immunized mice in $CO_2$ spleens were aseptically removed. A single cell suspension of pooled spleens was prepared. The spleen cells and the myeloma cells were washed several times with DMEM and fused twice in the presence of 1 ml 50% (w/v) PEG 3550 (ratio spleen cells to SP2/0 2.5:1 and 2.4:1). The hybridomas produced were resuspended in CGM containing 20% FCS and aminopterin (HAT medium). The cell suspension (140 Cl/well) of each fusion was plated out into eight 96-well tissue culture flat-bottom plates (Corning-Costar) containing 140 Cl/well peritoneal exudate cells as feeder cells in CGM with 20% FCS. The plates were incubated for 10 days. During this period cells were fed two times with HAT medium. An aliquot of the spleen cell preparation (about $8 \times 10^6$ spleen cells) was cultivated 10 days in a well of a 24-well plate and the cell culture supernatant served as positive control in ELISA.

1.6 Screening Assay

An ELISA was used for screening of IgG in cell culture supernatants. 96 well flat-bottom polystyrene microtiter plates (Greiner, Cat. No 655061) were coated with 50 µl/well PD-1Fc antigen (5 µg/ml) in 0.5 M carbonate/bicarbonate buffer, pH 9.6. After incubation overnight in a moist chamber at 4° C. the plates were washed with tris-buffered saline (TBS, 50 mM Tris, pH 7.8, 500 mM sodium chloride) containing 0.01% Triton X-100 (washing buffer) and blocked with 200 µl/well 2% FCS in TBS (blocking buffer) for 1 hour at room temperature (RT) on a shaker. The wells were washed with washing buffer and 100 µl cell culture supernatant was added in the appropriate well. Cell culture supernatant from SP 2/0 myeloma cells was used as a negative control. As positive control cell culture supernatant from spleen cell culture was used. The plates were incubated on a shaker for 1 h at RT, followed by several washes. For detection of bound antibodies plates were incubated with 50 µl/well goat anti-mouse IgG (Fab specific) conjugated to alkaline phosphatase (1:5000) in blocking buffer for 1 h at RT on a shaker, followed by several washes and addition of 150 µl/well substrate buffer (2 mM 4-nitrophenyl phosphate in 5% diethanolamine+0.5 mM $MgCl_2$, pH 9.8). The optical density (OD) was estimated in a 12-channel Dynex Opsys MR microplate reader at 405 nm. Wells with OD405 nm 2-fold higher than the OD405 nm of the average plate value were selected as positive.

1.7 Selection of Stable Antibody Producers

Cells from positive IgG producing cultures were transferred into wells of a 48-well plate and cultivated for several days (depending on the growth characteristics of the cells). An ELISA on PD-1Fc and without precoated antigen in order to select the specific binders was carried out. The cells from ELISA-positive wells were frozen in freezing medium (90% FCS, 10% DMSO). An aliquot of the cells was further cultivated for production of cell culture supernatants for further characterization.

1.8 Limiting Dilution Cloning

As soon as positive wells were identified, hybridoma cells were cloned to reduce the risk of overgrowth by non-producing cells (first cloning). To ensure that the antibodies are truly monoclonal the hybridomas were cloned again (second cloning). The method of limiting dilution was used for both cloning procedures. IgG producing cells were distributed into one 96 well plate containing feeder cells at a density of 1-3 cells per well. After 8-10 days (depending on growth characteristics) all plates were visually inspected under the microscope for detection of monoclonal growth. Culture supernatants from such wells were screened for specific immunoglobulin content using the above-described screening assay. The appropriate clones concerning growth characteristic and ELISA signal were selected, transferred into wells of a 24-well plate and cultivated for some days. A screening assay was performed. This procedure was repeated two to three times. The appropriate subclone was selected respectively for the second cloning procedure or cultivation for cryopreservation. This procedure resulted in the production of three anti-PD-1 antibodies: Clone 2, Clone 10 and Clone 19. Clone 2 is characterized only with respect to its epitope and binding off-rate.

Example 2

Characterization of the Clone 10 and Clone 19 Antibodies 2.1 Reagents Used for Characterization of the Properties of the Antibodies The following directly labelled antibodies were used: donkey anti-mouse IgG Alexa647 conjugate (Molecular Probes), anti-human CD4 Alexa647 conjugate (Serotec Ltd) and anti-human CD4 FITC conjugate (Serotec Ltd). OX7 ($mIgG_1$ culture supernatant; in-house) and MOPC21 ($mIgG_1$; Sigma-Aldrich Ltd) were used as isotype controls. Isotype-specific PE-labelled goat anti-mouse $IgG_1$ and $IgG_{2a}$ antibodies (STAR81PE and STAR82PE respectively) were obtained from Serotec Ltd and exhibited <1% cross reactivity with other murine Ig subclasses. Propidium iodide and rabbit IgG were from Sigma Ltd. Clone 19 anti-PD-1 antibody produced as described above was conjugated to Alexa647 using a kit following the manufacturer's instructions (Molecular Probes). IL-2 levels in cell culture supernatants were quantified using the DuoSet Human IL-2 ELISA Kit (R&D Systems Ltd).

2.2 Preparation and Isotyping of Antibodies

Hybridoma supernatant was prepared and diluted into sterile, azide-free PBS. Purified stocks of monoclonal antibodies were isotyped at 1 μg/ml in PBS using the IsoStrip Mouse Monoclonal Antibody Isotyping Kit (Santa Cruz; sc-24958). The isotypes of Clone 19, Clone 10 and Clone 2 were $IgG_{1K}$.

2.3 Epitope Mapping

Constructs encoding the human extracellular region of PD-1 with the transmembrane and intracellular regions of murine CD28 were cloned into the bi-cistronic mammalian expression vector pGFP2-n2 from BioSignal Packard Ltd, which also encodes GFP. Mutant constructs varying by one amino acid were prepared using the "drastic" mutagenesis approach (Davis el al. *Proc Natl Acad Sci USA*. 95, 5490-4 (1998)). Plasmids (2 μg/well) were transfected into HEK-293T cells in 6 well plates using Genejuice transfection reagent (Novagen; 6 μl/well). Mock and no-transfection controls were included with each experiment. Cells were harvested at 18-24 hours and stained with anti-PD1 antibodies or isotype controls at 10 μg/ml in PBS-azide for 1 h at 4° C. Cells were washed with PBS-Azide, pelleted at 1500 rpm/5 min and primary antibodies were labelled with Alexa647-conjugated donkey anti-mouse IgG (5 μg/ml) in PBS-Azide for 30 min at 4° C. Cells were washed as above and resuspended in 200 μl PBS-Azide before being analysed at the flow cytometer. Propidium iodide (5 μg/ml) was added immediately prior to analysis to identify dead cells. GFP-positive (transfected) viable cells were gated and analysed for binding of anti-PD1 antibodies. Mutants were defined as 'knock-out' (reducing the percentage of cells bound by the anti-PD1 antibody) or 'knock-down' (reducing the intensity of antibody staining relative to other PD-1 antibodies).

Figure 1:
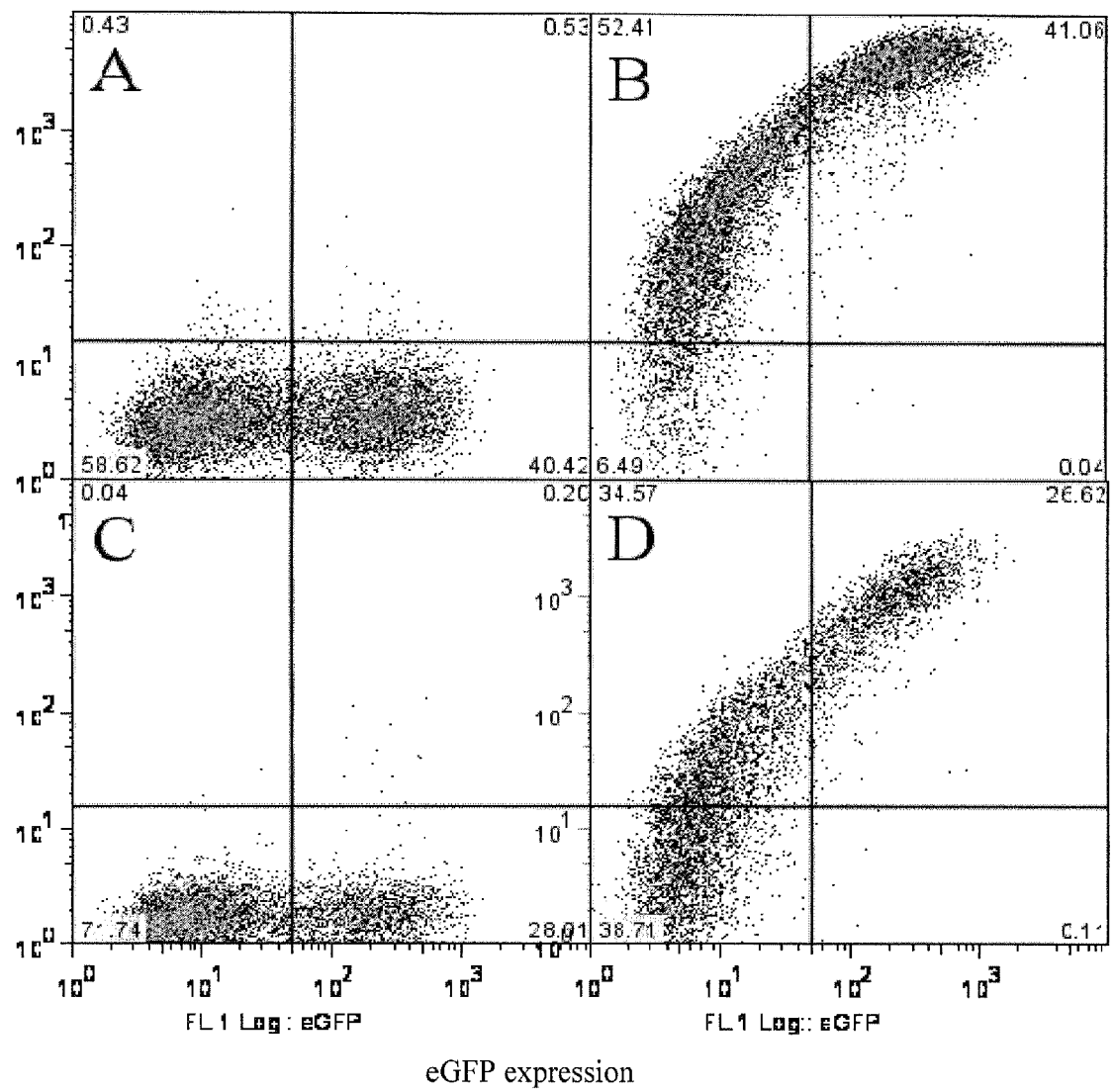
FIG. 1: Detection of antibody binding to human PD-1 transfectants. Cells were transfected with constructs expressing the extracellular region of human PD-1 (panels A and B) or mutants that affected the binding of Clone 19 (L16R; panel C) or Clone 10 (L103E; panel D) anti-PD-1 antibodies. The cells were labelled with isotype control antibody (panel A) or with Clone 19 (panels B and C) or Clone 10 (panel D) antibody, followed by Alexa647 labelled secondary antibody. Transfected 293T cells are eGFP-positive (x-axis). Antibody binding is shown on the y-axis.
Figure 2:
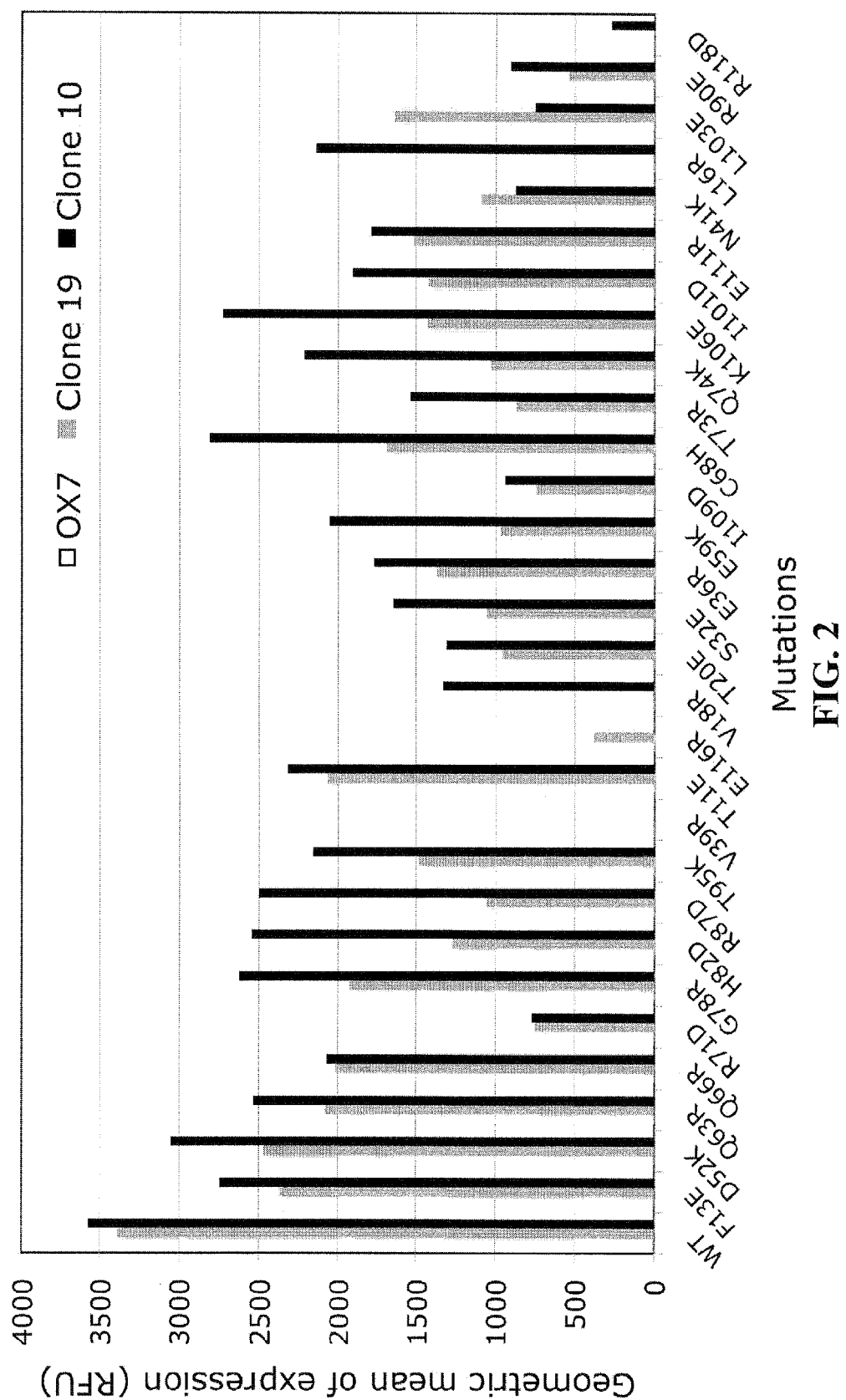
FIG. 2: PD-1 epitope screen. The geometric means of the Alex647 fluorescence levels for the GFP$^+$ cells is given for each of the mutants of PD-1, expressed as full length proteins in HEK 293T cells.

Following transfection, cells analysed at the flow cytometer were 85-90% viable by propidium iodide exclusion. An example of the binding analysis is shown in FIG. 1. Transfection efficiencies ranged from 15-50% ($GFP^+$). Isotype controls were negative on all transfectants. Analysis of the percentage of $GFP^+$ cells that are also positive for Alexa647 (anti-PD-1 antibody binding) shows that the L16R and R118D mutations completely eliminate Clone 19 binding (FIG. 2). All R118D expressing cells bind Clone 10, indicating functional expression of PD-1, but have the lowest intensity of all mutants (FIG. 2), suggesting a low level of expression. V18R partially eliminates Clone 19 binding. Clone 10 binds all the mutants but for mutants N41K and L103E the binding intensity for this antibody versus the other PD-1 antibodies is significantly decreased (FIG. 2). The binding analyses thus define two distinct epitopes each defined in turn by at least two residues: anti-PD-1 antibody Clone 10 binds to a membrane-distal epitope that overlaps with the ligand-binding region (Zhang et al. *Immunity* 20, 337-47 (2004)); Clone 19 binds to a membrane-proximal epitope. The binding-disrupting residues are mapped onto the murine PD-1 crystal structure in FIG. 3.

Example 3

Analysis of Clone 10- and Clone 19-Induced Signaling by a Dimeric Form of PD-1 with an Activating Cytoplasmic Domain To directly compare the signal-generating activities of the antibodies, a dimeric form of PD-1 was generated that consisted of the extracellular (antibody-binding) region of human PD-1 spliced to the transmembrane region of CD3ζ (to produce dimers) and the cytoplasmic region of CD28 (in order to have an "active" readout consisting of IL-2 secretion; FIG. 4A).

3.1 Construction of a Dimeric form of PD-1 for Detecting Anti-PD1 Antibody-Induced Activating Signaling in a T-Cell Hybridoma 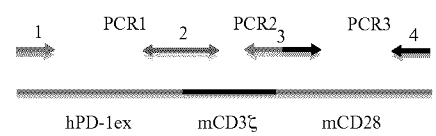 The hPD-1/mCD3ζWT/mCD28 construct was created in a series of five steps. In step 1, oligonucleotide 1 (left arrow; sequence 5'-TAGTAGAGATCTCTCAAGCAGGCCA CCATGCAAATCCCACAGGCGCCGTGG-3', SEQ ID NO: 33), which encodes a BglII restriction site and the rat ribosome binding site followed by the initiating codon and the first 21 bases of the signal peptide-encoding sequence of human PD-1, was used in a polymerase chain reaction (PCR1) with the complement of oligonucleotide 2 (5'-TCAGCCGGATCC TTCCAAACCCTGGTGCTCTGC-TACTTGCTAGATGG-3', SEQ ID NO: 34).

Oligonucleotide 2 encodes the last nine residues of the human PD-1 extracellular domain (up to residue 170 of the mature polypeptide) inserting a Bam H1 site, followed by 20 bases encoding the $NH_2$-terminal end of the mouse CD3ζ transmembrane domain. PCR reactions were carried out under standard conditions. In step 2, oligonucleotide 2 was used in a PCR reaction (PCR2) with the complement of oligonucleotide 3 (5'-ATCACAGCCCTGTACCTGAATAG-TAGAAGGAATAGACTC-3', SEQ ID NO: 35) which encodes the COOH-terminal end of the transmembrane region of mouse CD3ζ, followed by the first 21 bases encoding the $NH_2$-terminal end of the mouse CD28 cytoplasmic domain. In step 3, the PCR1 and PCR2 reaction products were purified, annealed, extended and then amplified in the presence of oligonucleotide 1 and the complement of oligonucleotide 3, to generate a cDNA encoding the extracellular region of PD-1 fused with the transmembrane region of CD3ζ. In step 4, oligonucleotide 3 was used in a PCR reaction (PCR3) with oligonucleotide 4 (5'-CTCGAGCTACTAGGGGCGG-TACGCTGCAAA-3', SEQ ID NO: 36), which encodes the COOH-terminal end of the cytoplasmic domain of mouse CD28 followed by a stop codon and a Xho I restriction site. In step 5, the purified PCR3 product was fused with the purified PCR product from step 3 by annealing the two products, extending the annealed hybrid, and then amplifying it with oligonucleotides 1 and 4.

Human PD-1 and mouse CD28 cDNA was amplified using pENTRhPD-1/mCD28 as template, which was originally constructed from IMAGE clones obtained from Geneservices Ltd (Cambridge UK). Mouse CD3ζ was amplified from DO11.10 mouse T cell hybridoma cDNA. The fusion PCR products were cloned into pCR4®-TOPO® (Invitrogen) and the final products sequenced by the dideoxy method. The constructs were cut with BglII and XhoI and inserted into the lentiviral vector pHR-SIN-BX-IRES-Em.

3.2 Detection of Activating Signaling by the hPD-1/mCD3ζWT/mCD28 Chimera

Figure 4A:
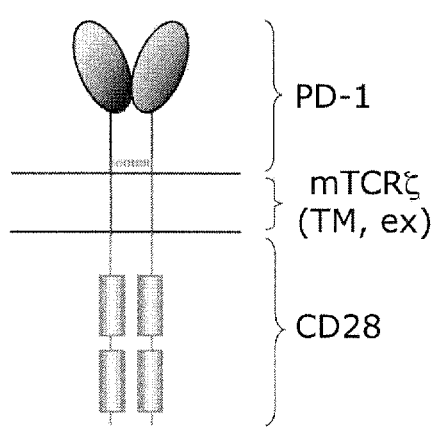
FIGS. 4A-4B: IL-2 secretion induced by anti-PD-1 antibodies binding to a hPD-1/mCD3ζWT/mCD28 chimera.
Figure 4B:
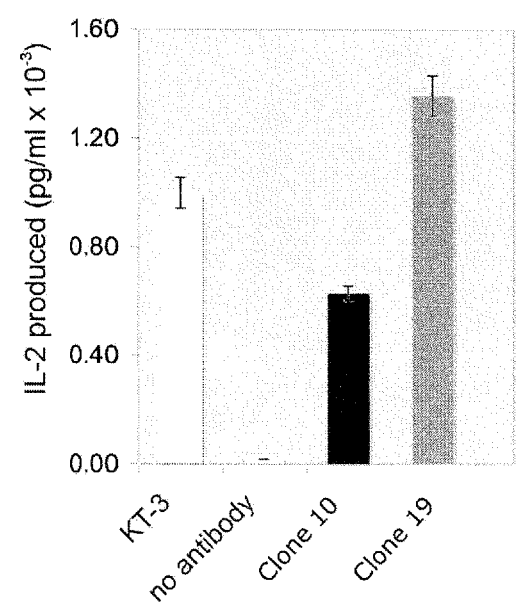

HEK 293T cells were transfected with pHR-SIN-BX-IRES-Em encoding hPD-1/mCD3ζWT/mCD28, and the supernatant used to infect DO11.10 T-cell hybridomas. Infected DO11.10 cells were propagated and FACS sorted for mouse PD-1 and EGFP expression, and then tested for agonistic signaling by the anti-PD-1 antibodies using IL-2 release as a stimulation assay readout. The IL-2 secretion results indicate that both antibodies are capable of inducing signaling via the hPD-1/mCD3ζWT/mCD28 chimera; however Clone 19, which binds PD-1 closest to the membrane induces the largest amount of IL-2 release (representative data is shown in FIG. 4B). This supports the notion that the topology of the complex formed by the antibodies is what determines the relative levels of signaling induced by agonists. The data also suggest that the degree of agonistic signaling can be varied with choice of antibody.

Example 4

Analysis of Inhibitory Signaling by Clone 10 and Clone 19 Antibodies in Human Peripheral Lymphocytes (PBL)

The antibodies were tested for their ability to inhibit TCR-derived activating signals by covalently coupling the antibodies, along with anti-CD3 antibodies, to tosyl-activated DYNALBEADS. The beads were then added to cultures of PBL labelled with carboxyfluorescein succinimidyl ester (CFSE). Proliferation levels were indicated by the fraction of cells with diluted CFSE determined by flow cytometric analysis.

4.1 Loading and Quantification of Antibody on DYNAL-BEADS

Figure 5:
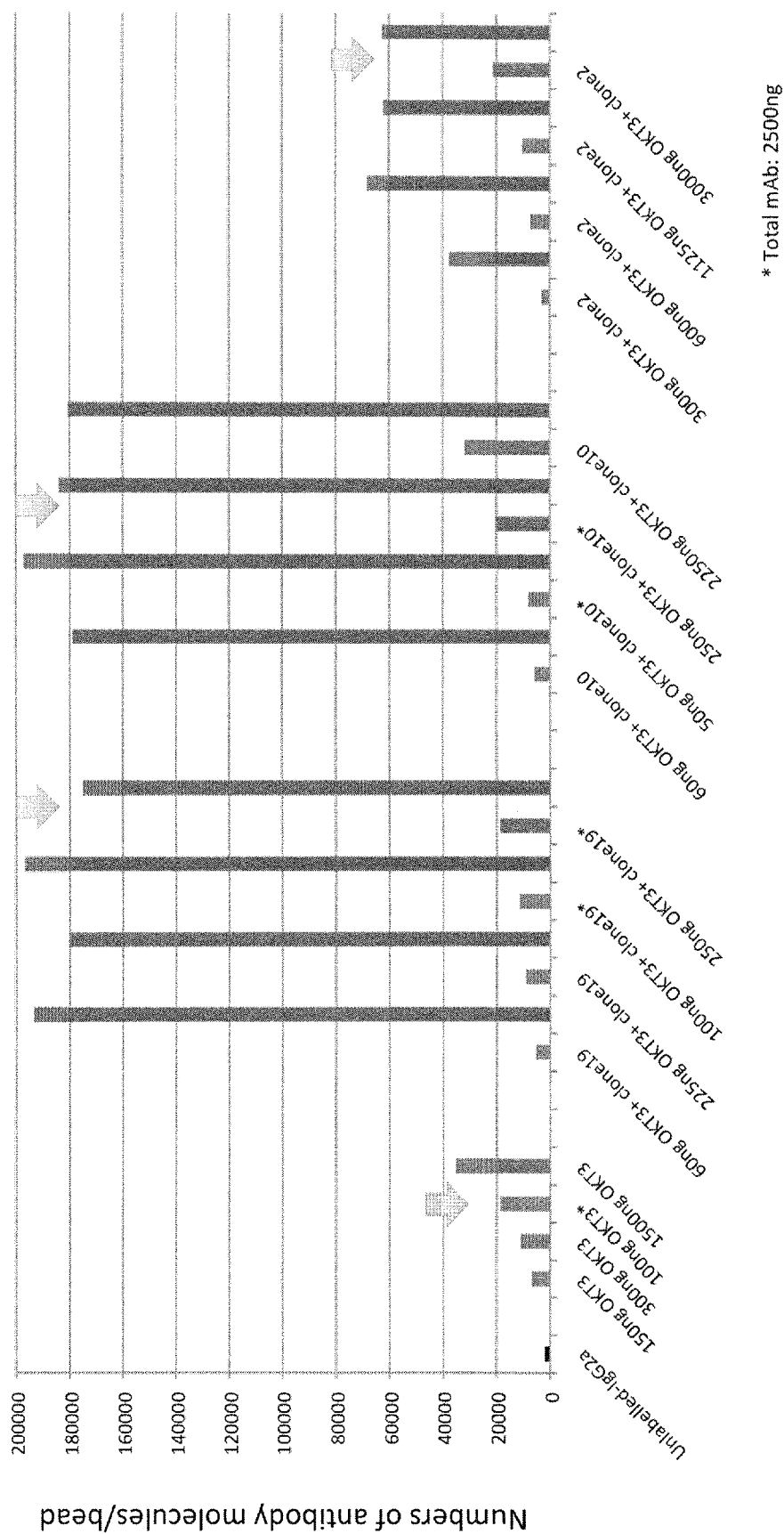
FIG. 5: Quantification of monoclonal antibodies loaded onto tosyl-activated DYNALBEADS. Amount of anti-human CD3 OKT3 antibody used per loading ($10^7$ beads with 2.5 μg total antibody) is shown on the x-axis. Remaining amount of antibody was made up with Rabbit IgG or anti-PD-1 antibodies (Clone 19, Clone 10, Clone 2) to a total of 2.5 μg. The number of IgG1 (Rabbit IgG or anti-PD-1 antibodies; red bars) or IgG2a (OKT3; blue bars) molecules detected per bead is shown on the y-axis. Green arrows indicate beads selected for use in the experiments shown in FIG. 6. Values are averages of duplicates.

Tosyl-activated 4.5 μm DYNALBEADS (M450; Invitrogen) were washed in 0.1M sterile phosphate buffer (pH 8) and loaded with 2.5 μg total antibody per $3 \times 10^7$ beads at 37° C. for 18-24 h with continuous inversion mixing. Rabbit IgG (Sigma) was used to equalise the amount of total antibody per bead-loading reaction. Beads were blocked for at least 30 min in RPMI with 10% FCS at room temperature and washed three times in serum-free RPMI. For some experiments, bead-bound antibody was quantified in duplicate with saturating amounts of isotype-specific PE-labelled goat antibodies and compared with Quantibrite™ prelabelled quantification kit (BD Biosciences Ltd.). The geometric mean fluorescence PE intensities of bead singlets (minus background of unloaded beads as a control) were used to calculate the absolute amount of antibody loaded per bead from the standard curve. An example of such a titration is given in FIG. 5. Loaded beads were stored at 4° C. During bead loading the amounts of anti-CD3 antibody added were varied so that, at the time of the experiments, the effects of matched sets of beads with near-equivalent levels of anti-CD3 antibody could be compared. The level of stimulation provided by anti-CD3 loaded beads was defined as low (resulting in 15% proliferation of bulk lymphocytes at day 5), medium-low (30% proliferation), medium-high (60% proliferation) and high (80% proliferation).

4.2 Proliferation Studies

Fresh heparinized blood was diluted 1:1 with PBS and the lymphocytes isolated by density gradient separation (Ficoll Hypaque). In some experiments, accessory cells were depleted by plastic adherence for 2 h at 37° C. or with specific antibody-labelled DYNALBEADS (against CD14/19/8/56). Cells were washed in PBS and RPMI and resuspended at $10^7$ cells/ml in serum-free RPMI. Cells were labeled with 25 μM CFSE in PBS for 10 min in the dark at RT. CFSE was quenched with an equal volume of FCS at RT for 5 min. Cells were washed 3-5 times with RPMI and resuspended at $10^6$ cells/ml in RPMI+10% FCS+PSG+2-ME (final concentration $5 \times 10^{-5}$ M). Antibodies (beads), mitogen or media was added to relevant wells in 96-well round-bottomed plates and $10^5$ cells/well were distributed and incubated at 37° C. for 3-5 days. For proliferation studies, cells were stained with directly-labelled cell-surface antibodies for 1 h at 4° C. Cells were washed with PBS-Azide, pelleted at 1500 rpm/5 min and resuspended in 200 μl PBS-Azide. Cells were analysed for CFSE and antibody labelling at the flow cytometer using FlowJo Flow Cytometry Analysis Software.

4.3 Effects of the Antibodies

Figure 6:
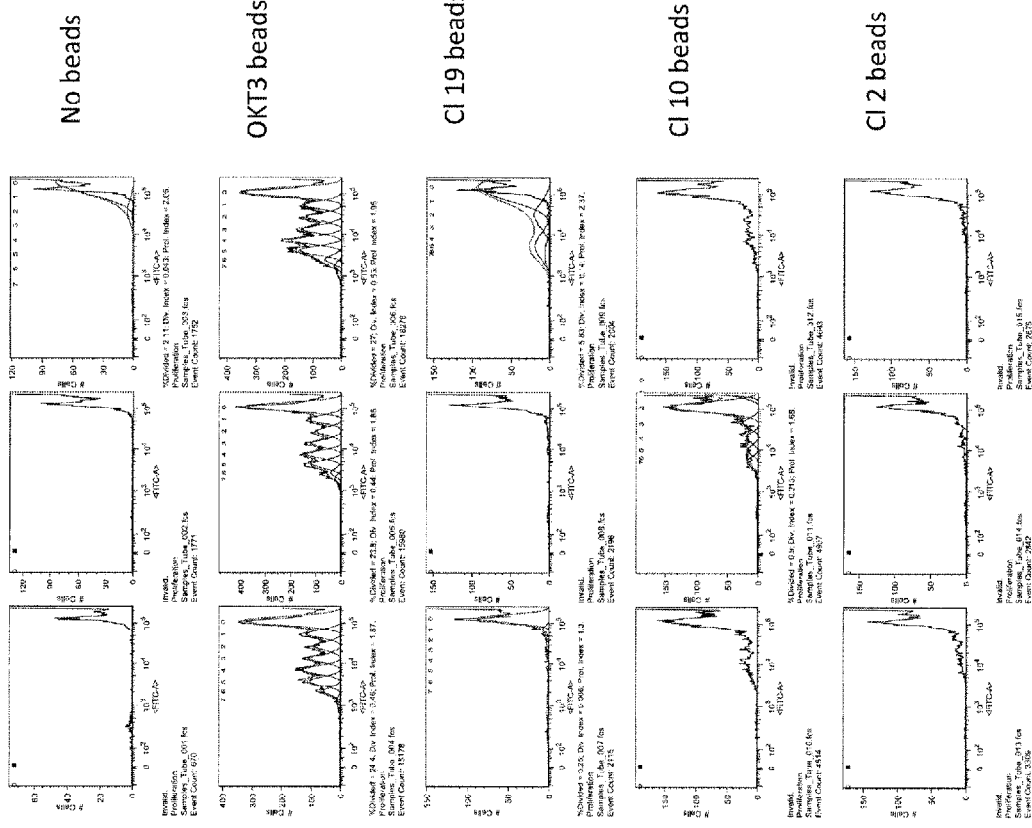
FIG. 6: Titration of anti-PD-1 antibodies coupled to tosyl-activated DYNALBEADS. Bulk preparations of PBL were incubated with beads containing anti-CD3 and increasing amounts of anti-PD-1 antibodies (Clone 19 or Clone 10). Amount of anti-PD-1 antibody loaded per $10^7$ beads (in a total of 2.5 μg mAb per $10^7$ beads) is shown on the x-axis. Proliferation (y-axis) was measured by CFSE dilution at day 5. Bars represent means of triplicates ±SD.

In the experimental results described in FIG. 6, the tosyl-activated beads used had been incubated with 2.5 μg of total antibody containing up to 2375 ng of anti-PD-1 Clone 10 or Clone 19 antibody, and enough anti-CD3 antibody to induce ~25% proliferation in the absence of anti-PD-1 antibody. Proliferation was measured by CFSE dilution at day 5. In experiment 1, visual inspection indicates that inhibition of proliferation is seen with all three antibodies, with Clones 2 and 19 now giving the highest levels of inhibition. For the data that can be analyzed using automated analysis software (FlowJo), the amount of inhibition of proliferation by Clone 19 is of the order of 80%. In experiment 2, although the degree of proliferation in the presence of OKT3 only is somewhat reduced (to ~15%), it is clear that Clones 2 and 19 are profoundly inhibiting proliferation; at most the cells that start proliferating undergo one or two rounds of proliferation only. Clone 10 is without any inhibitory effect in experiment 2.

Clone 10 antibodies were further tested for their ability to inhibit TCR-derived activating signals by covalently coupling the antibodies, along with anti-CD3 antibodies, to tosyl-activated DYNALBEADS. The beads were then added to cultures of human CD4+ T cells and proliferation measured by $^3$H-thymidine incorporation.

Tosyl-activated 4.5 μm DYNALBEADS (M450; Invitrogen) were washed in 0.1M sterile phosphate buffer (pH 7.5) and loaded with 2 μg of anti-human CD3 (clone OKT3) per $1 \times 10^7$ beads at 37° C. for 8 h with continuous inversion mixing. Beads were then washed to remove un-conjugated anti-CD3. Aliquots of the anti-CD3 conjugated beads were then secondarily coated with 3 μg of anti-PD-1 antibody or control per $1 \times 10^7$ beads at 37° C. for 19 h with continuous inversion mixing. Beads were washed and then incubated in 0.2M Tris/0.1% BSA (pH 8.5) for 3 hours to inactivate free tosyl groups, followed by washing and re-suspension of beads in PBS/0.1% BSA/2 mM EDTA (pH 7.4). Equal anti-CD3 and antibody coating of the bead sets was confirmed by staining the beads with fluorochrome-labelled isotype-specific antibodies and analysing by flow cytometry.

Fresh heparinized blood was diluted 1:1 with RPMI and the lymphocytes isolated by density gradient separation (Ficoll Hypaque). CD4+ T cells were purified from the whole PBLs by negative selection using MACS (CD4+ T cell isolation Kit II; Miltenyi Biotec). $1\times10^5$ human CD4+ T cells/well were cultured at a 1:1 ratio with the coated beads in 96-well round-bottomed plates and incubated at 37° C. for 6 days. Proliferation was measured at day 6 by addition of 0.5 µCi/well $^3$H-thymidine for the last 6 hours of culture. Cells were harvested onto glass-fibre filters and incorporated $^3$H-thymidine was measured by β-scintillation counting.

The results in FIG. 13 show the day 6 proliferative response by human CD4+ T cells measured in the presence of anti-CD3 plus Clone 10 antibody or control coated beads. The data are expressed as percentage of the maximal response (anti-CD3 plus BSA control) and are the mean of 4 different donor responses. CD4+ T cell proliferation was inhibited in the presence of Clone 10, so that the average proliferation observed was only 37.7% of the maximum.

Figure 8:
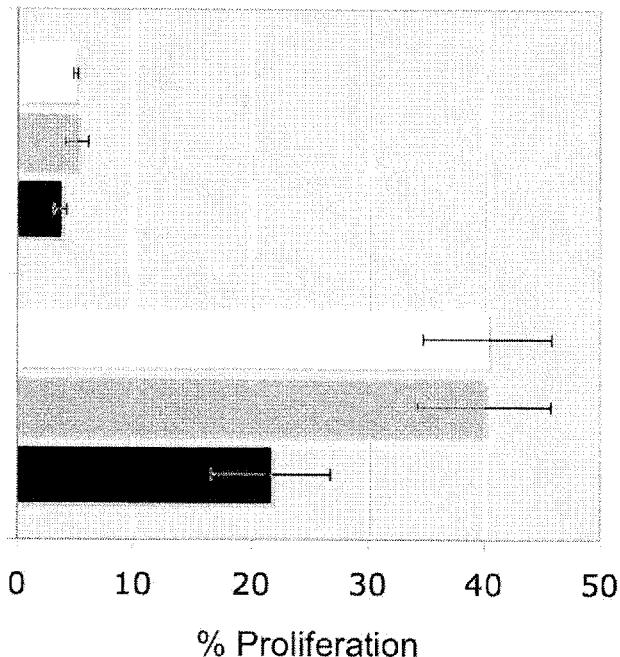
FIG. 8: Activation of T cells with beads quantified for Ig content. PBL were depleted of monocytes by plastic adherence (bulk PBL). The amount of anti-CD3 (OKT3) and anti-PD-1 antibodies (Clone 19 or Clone 10) was quantified and is shown in the table (left) expressed as number of molecules per bead. Proliferation (y-axis) was measured by CFSE dilution at day 5. Bars are duplicates ±SD.
Figure 9:
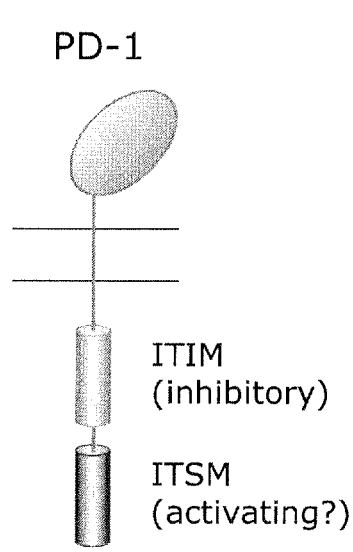
FIG. 9: Explanation for differential signaling by the two antibodies. Clone 19 induces stronger signaling by a hPD-1/mCD3ζWT/mCD28 chimera than Clone 10. PD-1 has ITIM (inhibitory, blue) and ITSM (activating, red) tyrosine-based signaling motifs. It is suggested that, in vitro, Clone 19 triggers the phosphorylation of both motifs whereas Clone 10 ligation results in phosphorylation of the inhibitory motif only, leading to more potent inhibitory signaling.

Clone 19 generally induces stronger signaling by the hPD-1/mCD3ζWT/mCD28 chimera than Clone 10 (FIG. 4B) but in some experiments it gives weaker inhibitory signaling by native PD-1 (see, e.g. FIG. 8). It is possible that this is because, in some experiments, Clone 19 but not Clone 10 ligation results in the phosphorylation of both the ITIM (inhibitory, blue) and the ITSM (activating, red) tyrosine-based signaling motifs of PD-1 (see FIG. 9).

Example 5

Using Two Antibodies with Non-Overlapping Epitopes to Enhance Signaling by a Monomeric Receptor Individual anti-PD-1 antibodies working alone, e.g. Clone 10, are already inhibitory but it should be possible to significantly enhance these effects by using pairs of anti-PD-1 antibodies. Initial characterization of the signaling properties of the antibodies relied on an assay in which PD-1 was expressed in the form of the hPD-1/mCD3ζWT/mCD28 chimera, which forms a homodimer. This was done in order to facilitate comparisons with anti-CD28 superagonistic antibodies, since CD28 is also a homodimer. A question that arises is: To what extent is signaling by the hPD-1/mCD3ζWT/mCD28 chimera dependent on its bivalency, and resulting cross-linking? To test this, a monomeric, monovalent form of PD-1, hPD-1/mCD28, that consisted of the extracellular (antibody-binding) and transmembrane regions of human PD-1 spliced to the cytoplasmic region of CD28 (in order to have an "active" readout consisting of IL-2 secretion; FIG. 10A), was generated.

5.1 Construction of a Monomeric Form of PD-1 for Detecting Anti-PD1 Antibody-Induced Activating Signaling in a T-Cell Hybridoma

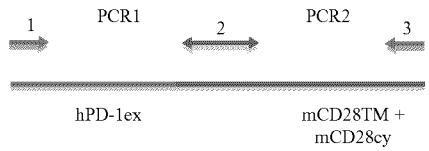

The hPD-1/mCD28 construct was created in a series of three steps. In step 1, oligonucleotide 1 (left arrow; sequence 5'-TAGTAGAGATCTCTCAAGCAGGCCACCAT GCAAATCCCACAGGCGCCGTGG-3', SEQ ID NO: 33), which encodes a BglII restriction site and the rat ribosome binding site followed by the initiating codon and the first 24 bases of the signal peptide-encoding sequence of human PD-1, was used in a polymerase chain reaction (PCR1) with the complement of oligonucleotide 2 (5'-GCCCAGCCGGC-CAGTTCC AAACCTTTTGGGTGCTGGTGGTGGT-TGGT-3', SEQ ID NO: 37). Oligonucleotide 2 encodes the last 23 bases of the human PD-1 extracellular domain (up to residue 149 of the mature polypeptide), followed by 24 bases encoding the $NH_2$-terminal sequence of the mouse CD28 transmembrane region. PCR reactions were carried out under standard conditions. In step 2, oligonucleotide 2 was used in a PCR reaction (PCR2) with the complement of oligonucleotide 3 (5'-TTTGCAGCGTACCGCCCCACGCGTTAG-TAGCTCGAG-3', SEQ ID NO: 38) which encodes the COOH-terminal end of the cytoplasmic domain of mouse CD28, a Mlu I restriction site followed by a stop codon and a Xho I restriction site. In step 3, the purified PCR2 product was fused with the purified PCR1 product from step 1 by annealing the two products, extending the annealed hybrid, and then amplifying it with oligonucleotides 1 and 3.

Mouse CD28 sequence was amplified using pCR4®-TOPO®rCD28/mCD28 as template, which was originally amplified from DO11.10 mouse T cell hybridoma cDNA. The human extracellular PD-1 was amplified from pE14hPD-1Long, a gift from Dr Chao Yu of the MRC Human Immunology Unit, Oxford. The fusion PCR products were cloned into pCR4®-TOPO®(Invitrogen) and the final products sequenced by the dideoxy method. The constructs were cut with BglII and XhoI and inserted into the lentiviral vector pHR-SIN-BX-IRES-Em for infection of DO11.10 cells. Activation of the DO11.10 cells expressing the hPD-1/mCD28 chimera by anti-PD-1 antibodies was examined using IL-2 secretion as a read-out.

Figure 3:
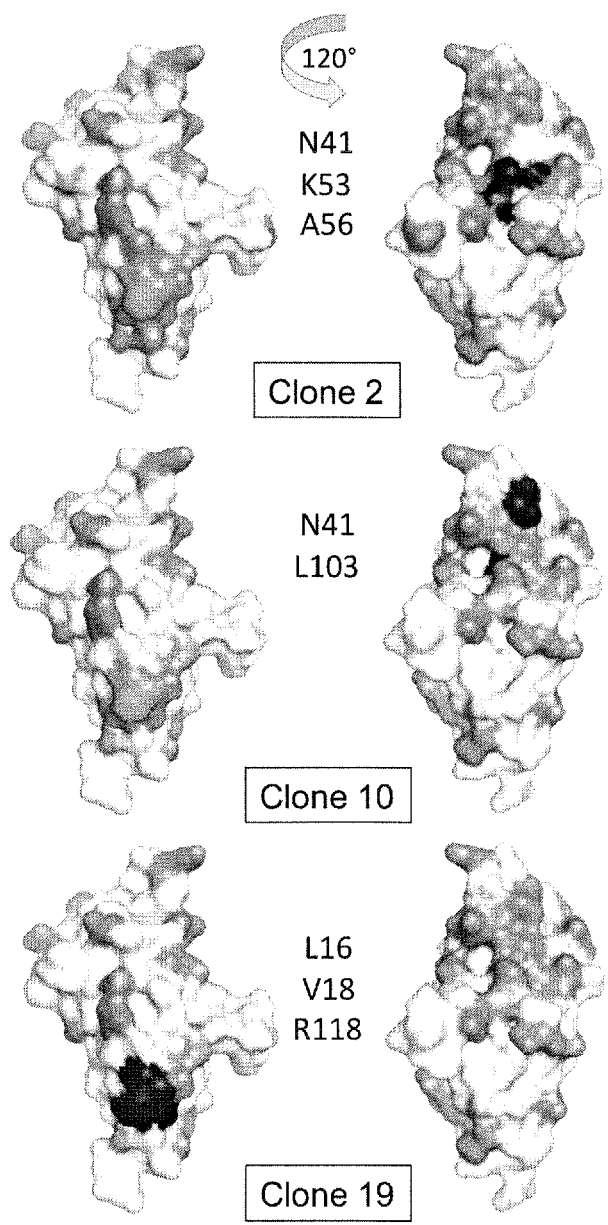
FIG. 3: Anti-PD-1 antibody epitopes. The epitopes were mapped by antibody binding analysis following expression of single-residue mutated forms of PD-1 in HEK 293T cells. Mouse PD-1 residues equivalent to human PD-1 residues that when mutated partially or fully block the binding of Clones 2, 10 and 19 antibody are highlighted in black on the mouse PD-1 crystal structure (Zhang et al. *Immunity* 20, 337-47 (2004)). Mouse-equivalents of human PD-1 residues that have no effect on the binding of the antibodies when mutated are coloured grey. The mutated residue numbers for the non-binding mutants are given alongside the structure, for each antibody. Clone 2 and clone 10 antibodies appear to compete with one another for binding to PD-1 based upon the results of this analysis.

5.2 Lack of Signaling by hPD-1/mCD28 Suggests that Agonistic Signaling May be Enhanced by Cross-Linking a Monomeric Receptor with Two Antibodies that Bind to Non-Overlapping Epitopes Clone 10 and Clone 19 were not agonistic for a chimeric form of human PD-1, i.e. hPD-1/mCD28, consisting of the monomeric extracellular region of PD-1 attached to the transmembrane and intracellular signaling domains of CD28 (FIG. 10), in contrast to the equivalent CD28 construct (containing the homodimeric extracellular domain of rat CD28). The likeliest explanation for this is that, because PD-1 is monomeric and CD28 is a homodimer, the attachment of bivalent antibody leads to the assembly of a multimeric array of "cross-linked" CD28 molecules and a very high density of signaling domains (FIG. 11A), whereas the binding of Clone 10 or Clone 19 brings together only pairs of PD-1 molecules (FIG. 11B). In vivo, therefore, antibodies binding to homodimeric receptors will generally produce stronger signaling than an antibody that binds to a monomeric receptor. In the case of PD-1, if a multimeric assembly of PD-1 molecules could be generated this would be predicted to lead to much more potent signaling (FIG. 11C). The positions of the epitopes of Clone 10 (or Clone 2) and of Clone 19 on opposite "sides" of PD-1 (FIG. 3) imply that the two antibodies are likely to bind to non-overlapping surfaces, i.e. that each native PD-1 monomer would be capable of binding both antibodies. This suggests that pairs of the antibodies could be used in vivo to "cross-link" native PD-1 monomers as shown in FIG. 11C. The high-density arrays of sequestered PD-1 molecules thus generated are expected to produce more potent signaling than would be possible using single antibodies.

5.3 Agonistic Signalling is Enhanced by Cross-Linking a Monomeric Receptor with Two Antibodies that Bind to Non-Overlapping Epitopes To test the idea that pairs of antibodies could be used to "cross-link" native PD-1 monomers and induce enhanced agonistic signaling, DO11.10 cells expressing the hPD-1/mCD28 chimeric protein were used in a Clone 10/Clone 19 antibody stimulation assay as follows. 96-well flat-bottomed plates (Costar EIA/RIA plates) were coated overnight at 4° C. with 500 μg/ml donkey anti-mouse IgG (Jackson Immunoresearch) in coating buffer (15 mM Na2CO3, 35 mM NaHCO3, pH 9.6. Prior to the addition of cells, the plates were washed three times with 200 μl chilled PBS. $5 \times 10^5$ cells were centrifuged at 1200 rpm for 3 minutes and resuspended in 100 μl complete medium containing the Clone 19 antibody at various concentrations for 30 minutes. The cells then washed and subjected to an additional 30 minute incubation with Clone 10 at various concentrations, before the cells were plated out in triplicate onto the donkey anti-mouse IgG pre-coated 96 well plates. Cells were incubated at 37° C., in 5% CO2 for 48 hours before the cell culture supernatant was removed and assayed for mouse interleukin-2 (IL-2) by ELISA.

Figure 7:
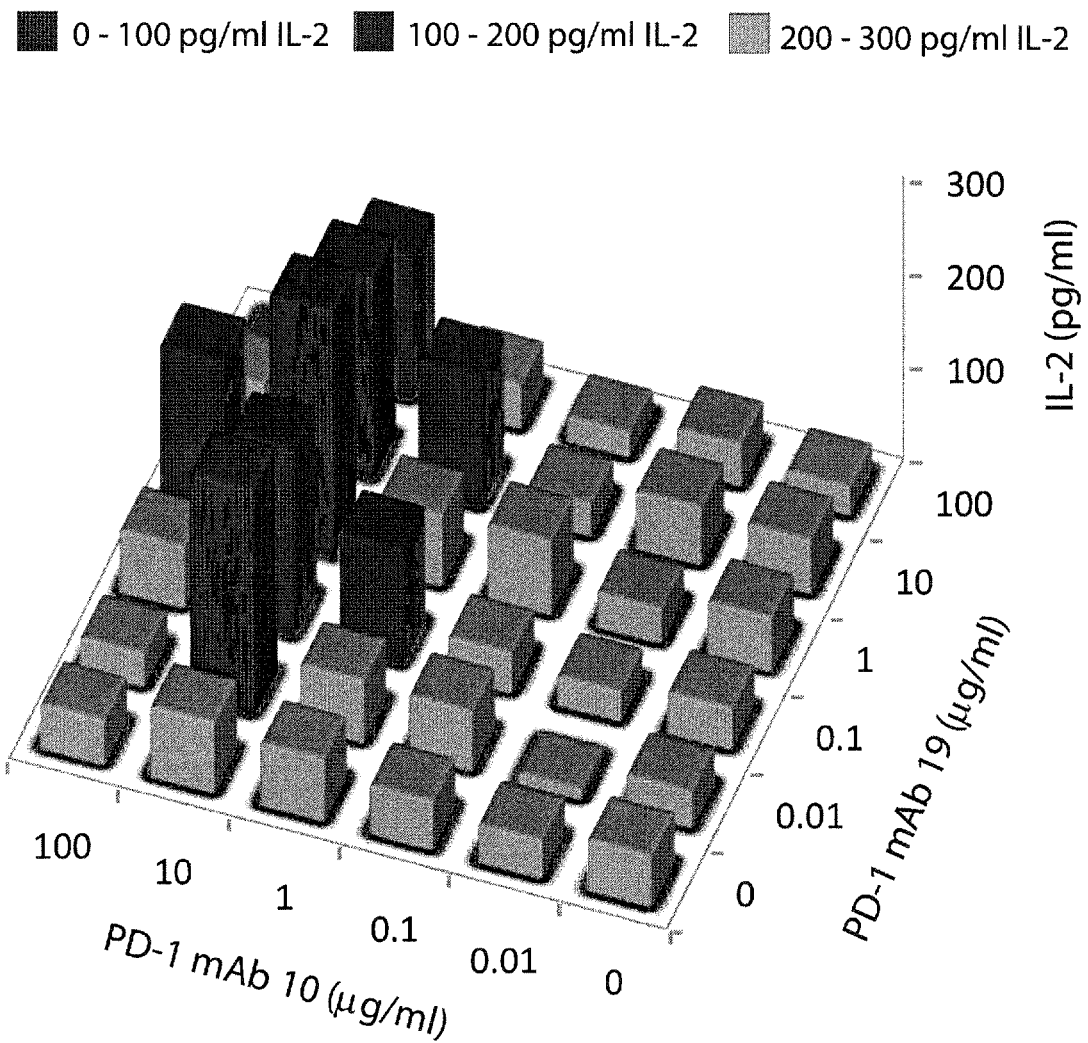
FIG. 7: Stimulation of a PD-1/mCD28 chimera-expressing DO11.10 cell line with titrations of two anti-PD-1 antibodies. DO11.10 cells expressing a PD-1/mCD28 chimera were incubated with titrations of anti-PD-1 Clone 19 antibody (from 100 μg/ml to 0 μg/ml) and anti-PD-1 Clone 10 antibody (from 100 μg/ml to 0 μg/ml). Cells were then incubated in donkey anti-mouse IgG antibody coated (500 μg/ml) 96 well plates for 48 hours before tissue culture supernatant was assayed for IL-2 by ELISA.

The results of this experiment (FIG. 7) show that at the highest concentrations, i.e. 100 μg/ml, neither Clone 10 nor Clone 19 initiate signalling (IL-2 production) in DO11.10 cells expressing the hPD-1/mCD28 chimeric protein. However, successive incubations of the antibodies at 10-100 μg/ml induced significant levels of IL-2 production. This suggests that cross-linking pairs of antibodies could be used to induce enhanced signalling in vivo.

Sequence Information for Clones 2, 10 and 19
Antibodies (CDRs Indicated by Underlining in
Amino Acid Sequences)

```
Clone 2
VK DNA
                                        (SEQ ID NO: 1)
gacattgtgctgacacagtctcctgcttctttagctgtatctctgg
ggcagagggccaccatctcatgcagggccagcaaaagtgtcagtac
atctggctttaattatatacactggtaccaacagaaaccaggacag
ccacccaaactcctcatctatcttgcatccaacctagaatctgggg
tccctgccaggttcagtggcagtgggtctgggacagacttcaccct
caacatccatcctgtggaggacgaggatgctgcaacctattactgt
cagcacagtagggagcttccgctcacgttcggtgctgggaccaagc
tggaaataaaa VK protein
                                        (SEQ ID NO: 2)
DIVLTQSPASLAVSLGQRATISCRASKSVSTSGFNYIHWYQQKPGQ
PPKLLIYLASNLESGVPARFSGSGSGTDFTLNIHPVEDEDAATYYC
QHSRELPLTFGAGTKLEIK VH DNA (original cloned)
                                        (SEQ ID NO: 3)
caggtccaactgcagcagcctggggctgaactggtgaagcctgggg
cttcagtgaagttgtcctgcaaggcttctggctacaccttcaccac
ctactatttgtactgggtgaggcagaggcctggacaaggccttgag
tggattgggggggattaatcctagcaatggtggtactaacttcaatg
agaagttcaagagcaaggccacactgactgtagacaaatcctccag
cacagcctacatgcaactcaacagcctgacatctgaggactctgcg
gtctattactgtacaagacgggactataggtacgacagaggctttg
actactggggccaaggcacctcagtcacagta VH DNA (mutated to remove splice site)
                                        (SEQ ID NO: 5)
caggtccaactgcagcagcctggggctgaactggtgaagcctgggg
cttcagtgaagttgtcctgcaaggcttctggctacaccttcaccac
ctactatttgtactgggtgaggcagaggcctggacaaggccttgag
tggattgggggggattaatcctagcaatggtggtactaacttcaatg
agaagttcaagagcaaggccacactgactgtagacaaatcctcctc
tacagcctacatgcaactcaacagcctgacatctgaggactctgcg
gtctattactgtacaagacgggactataggtacgacagaggctttg
actactggggccaaggcacctcagtcacagtc VH protein
                                (SEQ ID NO: 4 or SEQ ID NO: 6)
QVQLQQPGAELVKPGASVKLSCKASGYTFTTYYLYWVRQRPGQGLE
WIGGINPSNGGTNFNEKFKSKATLTVDKSSSTAYMQLNSLTSEDSA
VYYCTRRDYRYDRGFDYWGQGTSVTV Clone 10
VK DNA
                                        (SEQ ID NO: 7)
gatgttttgatgacccaaactccactctccctgcctgtcagtcttgg
agatcaagcctccatctcttgcagatctggtcagaacattgtacata
gtaatggaaacacctattagaatggtacctacagaaaccaggccag
tctccaaagctcctgatctacaaagtctccaaccgatttttggggt
cccagacaggatcagtggcagtggatcagggacagatttcacactca
agatcagcagagtggaggctgaggatctgggagtttatttctgcttt
caaggttcacatgttccattcacgttcggctcggggacaaagctgga
aataaaa VK protein
                                        (SEQ ID NO: 8)
DVLMTQTPLSLPVSLGDQASISCRSGQNIVHSNGNTYLEWYLQKPGQ
SPKLLIYKVSNRFFGVPDRISGSGSGTDFTLKISRVEAEDLGVYFCF
QGSHVPFTFGSGTKLEIK VH DNA
                                        (SEQ ID NO: 9)
gatgtgcagcttcaggagtcgggacctggcctggtgaaaccttctca
gtctctgtccctcacctgcactgtcactggctactcaatcaccagtg
attatgcctggaactggatccggcagtttccaggaaacaaactggag
tggatgggctacataaactacagtggtagcactagctacaacccatc
tctcaaaagtcgaatctctatcactcgagacacatccaagaaccagt
tcttcctgcagttgaattctgtgactactgaggacacagccacatat
tactgtgcaagatggatcggtagtagcgcctggtacttcgatgtctg
gggcgcagggaccacggtcacagtc VH protein
                                        (SEQ ID NO: 10)
DVQLQESGPGLVKPSQSLSLTCTVTGYSITSDYAWNWIRQFPGNKLE
WMGYINYSGSTSYNPSLKSRISITRDTSKNQFFLQLNSVTTEDTATY
YCARWIGSSAWYFDVWGAGTTVTV Clone 19
VK DNA
                                        (SEQ ID NO: 11)
gaaaatgtgctcacccagtctccagcaatcatgtctgcatctccagg
ggaaaaggtcaccatgacctgcagggccagctcaagtgtaatttcca
gttacttgcactggtaccagcagaagtcaggtgcctccccaaactc
tggatttatagcacttccaacttggcttctggagtccctgatcgctt
cagtggcagtgggtctgggacctcttactctctcacaatcagcagtg
tggaggctgaagatgctgccacttattactgccagcagtacaatggt
tacccgctcacgttcggtgctgggaccaagctggaaataaaa VK protein
                                        (SEQ ID NO: 12)
ENVLTQSPAIMSASPGEKVTMTCRASSSVISSYLHWYQQKSGASPKL
WIYSTSNLASGVPDRFSGSGSGTSYSLTISSVEAEDAATYYCQQYNG
YPLTFGAGTKLEIK VH DNA
                                        (SEQ ID NO: 13)
caggttcagctacagcagtctggggctgagctggtgaagcctgggc
ctcagtgaagatgtcctgcaaggcttttggctacaccttcactacct
atccaatagagtggatgaagcagaatcatgggaagagcctagagtgg
attggaaattttcatccttacaatgatgatactaagtacaatgaaaa
attcaagggcaaggccaaattgactgtagaaaaatcctctaccacag
tctacttggagctcagccgattaacatctgacgactctgctgtttat
tactgtcaagggagaactacggtagtcacgggggttttgtttactg
gggccaagggactctggtcaccgtc
```

VH protein
(SEQ ID NO: 14)
QVQLQQSGAELVKPGASVKMSCKAF<u>GYTFTTTYPIE</u>WMKQNHGKSLEW
IGN<u>FHPYNDDTKYNEKFKG</u>KAKLTVEKSSTTVYLELSRLTSDDSAVY
YCAR<u>ENYGSHGGFVY</u>WGQGTLVTV

TABLE 1

CDR SEQUENCES FOR CLONES 2, 10 AND 19 ANTIBODIES

| | CDR1 | CDR2 | CDR3 |
|---|---|---|---|
| Clone 2 Vκ | RASKSVSTSGFNYIH (SEQ ID NO: 15) | LASNLES (SEQ ID NO: 16) | QHSRELPLT (SEQ ID NO: 17) |
| Clone 2 VH | GYTFTT<u>YYLY</u> (SEQ ID NO: 18) | GINPSNGGT NFNEKFKS (SEQ ID NO: 19) | RDYRYDRGFDY (SEQ ID NO: 20) |
| Clone 10 Vκ | RSGQNIVHSNGNTYLE (SEQ ID NO: 21) | KVSNRFF (SEQ ID NO: 22) | FQGSHVPFT (SEQ ID NO: 23) |
| Clone 10 VH | GYSIT<u>SDYAWN</u> (SEQ ID NO: 24) | YINYSGST SYNPSLKS (SEQ ID NO: 25) | WIGSSAWYFDV (SEQ ID NO: 26) |
| Clone 19 Vκ | RASSSVISSYLH (SEQ ID NO: 27) | STSNLAS (SEQ ID NO: 28) | QQYNGYPLT (SEQ ID NO: 29) |
| Clone 19 VH | GYTFT<u>TYPIE</u> (SEQ ID NO: 30) | NFHPYNDD TKYNEKFKG (SEQ ID NO: 31) | ENYGSHGGFVY (SEQ ID NO: 32) |

In Table 1 and the sequences provided above, the heavy chain CDR1s for clones 2, 10 and 19 have been identified according to both the combined Kabat/Chothia numbering system and the Kabat numbering system. All other CDRs have been identified according to the Kabat numbering system (Kabat et al., 1987, "In sequences of proteins of immunological interest", U.S. Dept. Health and Human Services, NIH USA. Heavy chain CDR1s for clones 2, 10 and 19, as identified by the Kabat numbering system, are identified (underlined amino acids) in Table 1.

We claim:

1. An isolated antibody selected from:
   a) a monoclonal antibody that binds PD-1 and is produced by the hybridoma clone 10 or antigen binding fragment thereof, said hybridoma clone being deposited with the European Collection of Cell Cultures (ECACC) under accession number 08090902;
   b) an isolated antibody that binds PD-1 or antigen binding fragment comprising SEQ ID NO: 8 and SEQ ID NO: 10; or
   c) a bispecific, humanized, single-chain, chimeric, synthetic or recombinant antibody that binds PD-1 comprising a light chain variable region comprising SEQ ID NO: 21 (light chain CDR1), SEQ ID NO: 22 (light chain CDR2), SEQ ID NO: 23 (light chain CDR3) and a heavy chain variable region comprising SEQ ID NO: 24 (heavy chain CDR1), SEQ ID NO: 25 (heavy chain CDR2) and SEQ ID NO: 26 (heavy chain CDR3).

2. A pharmaceutical composition comprising an antibody or antigen binding fragment according to claim 1.

3. The isolated antibody according to claim 1, wherein said antibody comprises a light chain variable region comprising SEQ ID NO: 21 (light chain CDR1), SEQ ID NO: 22 (light chain CDR2), SEQ ID NO: 23 (light chain CDR3) and a heavy chain variable region comprising SEQ ID NO: 24 (heavy chain CDR1), SEQ ID NO: 25 (heavy chain CDR2) and SEQ ID NO: 26 (heavy chain CDR3).

4. The isolated antibody according to claim 1, wherein said antibody is the monoclonal antibody produced by the hybridoma clone 10 or an antigen binding fragment thereof, said hybridoma clone being deposited with the European Collection of Cell Cultures (ECACC) under accession number 08090902.

5. The isolated antibody according to claim 1, wherein said antibody comprises a bispecific, humanized, single-chain, chimeric, synthetic or recombinant antibody comprising a light chain variable region comprising SEQ ID NO: 21 (light chain CDR1), SEQ ID NO: 22 (light chain CDR2), SEQ ID NO: 23 (light chain CDR3) and a heavy chain variable region comprising SEQ ID NO: 24 (heavy chain CDR1), SEQ ID NO: 25 (heavy chain CDR2) and SEQ ID NO: 26 (heavy chain CDR3).

6. The pharmaceutical composition according to claim 2, wherein said antibody is a monoclonal antibody that binds PD-1 and is produced by the hybridoma clone 10 or an antigen binding fragment thereof, said hybridoma clone being deposited with the European Collection of Cell Cultures (ECACC) under accession number 08090902.

7. The pharmaceutical composition according to claim 2, wherein said antibody or antigen binding fragment comprises SEQ ID NO: 8 and SEQ ID NO: 10.

8. The pharmaceutical composition according to claim 2, wherein said antibody is a bispecific, humanized, single-chain, chimeric, synthetic or recombinant antibody comprising a light chain variable region comprising SEQ ID NO: 21 (light chain CDR1), SEQ ID NO: 22 (light chain CDR2), SEQ ID NO: 23 (light chain CDR3) and a heavy chain variable region comprising SEQ ID NO: 24 (heavy chain CDR1), SEQ ID NO: 25 (heavy chain CDR2) and SEQ ID NO: 26 (heavy chain CDR3).

9. The isolated antibody according to claim 1, wherein said antibody is tagged with a detectable label.

10. The isolated antibody according to claim 9, wherein said detectable label is a radiolabel or an enzyme.

* * * * *

UNITED STATES PATENT AND TRADEMARK OFFICE
CERTIFICATE OF CORRECTION

PATENT NO. : 8,927,697 B2  
APPLICATION NO. : 13/062559  
DATED : January 6, 2015  
INVENTOR(S) : Simon Davis et al.

Page 1 of 1

It is certified that error appears in the above-identified patent and that said Letters Patent is hereby corrected as shown below:

In The Specification

Column 10,
Line 39, "region (Fe)," should read --region (Fc),--.

Column 19,
Line 60, "actactggggccaaggcacctcagtcacagta" should read
--actactggggccaaggcacctcagtcacagtc--.

Signed and Sealed this
Tenth Day of November, 2015

Michelle K. Lee
*Director of the United States Patent and Trademark Office*